(12) United States Patent
Mueller et al.

(10) Patent No.: US 6,554,794 B1
(45) Date of Patent: Apr. 29, 2003

(54) NON-DEFORMING DEFLECTABLE MULTI-LUMEN CATHETER

(76) Inventors: Richard L. Mueller, 2305 Cypress Point, Byron, CA (US) 94514; U. Hiram Chee, 127 Dolton Ave., San Carlos, CA (US) 94070; Steven A. Daniel, 40874 Calido Pl., Fremont, CA (US) 94539; Amr Salahieh, 935 Lovell Ave., Campbell, CA (US) 95008; Robert LaDuca, 150 Davenport Landing Rd., Davenport, CA (US) 95017; Lauren K. Lundquist, 1941 W Edmundson Ave., Morgan Hill, CA (US) 95037; Richard D. Phipps, 16610 Oak View Cir., Morgan Hill, CA (US) 95037; Daniel S. Brown, 268 Carlton Ave., Los Gatos, CA (US) 95032

( * ) Notice: Subject to any disclaimer, the term of this patent is extended or adjusted under 35 U.S.C. 154(b) by 0 days.

(21) Appl. No.: 09/326,118

(22) Filed: Jun. 4, 1999

Related U.S. Application Data

(63) Continuation-in-part of application No. 09/156,963, filed on Sep. 18, 1998, and a continuation-in-part of application No. 09/156,964, filed on Sep. 18, 1998, now Pat. No. 6,179,809, and a continuation-in-part of application No. 09/080,175, filed on May 16, 1998, now Pat. No. 6,183,444.
(60) Provisional application No. 60/059,892, filed on Sep. 24, 1997.

(51) Int. Cl.[7] .......................... A61M 37/00; A61B 18/18
(52) U.S. Cl. .................... 604/95.04; 604/528; 604/532; 606/15
(58) Field of Search ............... 606/2, 7, 13, 15; 604/95.01, 95.04, 528, 532; 600/146, 434

(56) References Cited

U.S. PATENT DOCUMENTS 3,890,977 A 6/1975 Wilson
4,350,148 A 9/1982 Sivak, Jr. et al.
4,475,905 A 10/1984 Himmelstrup
4,586,923 A 5/1986 Gould et al.
4,658,817 A 4/1987 Hardy
4,669,465 A 6/1987 Moore et al.
4,702,260 A 10/1987 Wang
4,766,906 A 8/1988 Wang
4,784,133 A 11/1988 Mackin
4,844,062 A 7/1989 Wells
4,846,171 A 7/1989 Kauphusman et al.
4,911,148 A 3/1990 Sosnowski et al.
4,920,980 A 5/1990 Jackowski
4,960,134 A 10/1990 Webster, Jr.
4,976,710 A 12/1990 Mackin
5,030,204 A 7/1991 Badger et al.

(List continued on next page.)

FOREIGN PATENT DOCUMENTS

EP 0 515 867 A2 12/1992
EP 0 900 547 A1 3/1999

(List continued on next page.)

OTHER PUBLICATIONS

"Structure and Properties of Ti–Ni Alloys," Duerig, T.W. and A. R. Pelton. In Press, Titanium Handbook, ASM 1994.

(List continued on next page.)

Primary Examiner—Roy D. Gibson
(74) Attorney, Agent, or Firm—Gibson, Dunn & Crutcher LLP

(57) ABSTRACT

A non-deforming deflectable multi-lumen catheter with an outer jacket having a deflectable distal end portion, an eccentric pull wire lumen, coil and shim embedded therein. The deflectable distal portion optionally having one or more transaxial notches in the external surface of the outer jacket. A functional device is disposed within the lumen of an inner tube substantially coaxial with the outer jacket of the catheter. The distal tip of the functional device egressible from the distal tip of the catheter, and upon deflection, automatically aligns with the distal tip of the catheter and functional device.

73 Claims, 25 Drawing Sheets

U.S. PATENT DOCUMENTS

| | | | |
|---|---|---|---|
| 5,104,393 A | | 4/1992 | Isner et al. |
| 5,114,402 A | | 5/1992 | McCoy |
| 5,125,896 A | | 6/1992 | Hojeibane |
| 5,178,158 A | | 1/1993 | de Toledo |
| 5,190,050 A | | 3/1993 | Nitzsche |
| 5,255,679 A | | 10/1993 | Imran |
| 5,261,889 A | | 11/1993 | Laine et al. |
| RE34,502 E | | 1/1994 | Webster, Jr. |
| 5,279,596 A | | 1/1994 | Castaneda et al. |
| 5,307,803 A | | 5/1994 | Matsuura et al. |
| 5,358,479 A | | 10/1994 | Wilson |
| 5,364,352 A | * | 11/1994 | Cimino et al. ................ 604/95 |
| 5,378,234 A | * | 1/1995 | Hammerslag et al. ........ 604/95 |
| 5,380,316 A | | 1/1995 | Aita et al. |
| 5,386,837 A | | 2/1995 | Sterzer |
| 5,389,096 A | | 2/1995 | Aita et al. |
| 5,397,304 A | | 3/1995 | Truckai |
| 5,409,453 A | | 4/1995 | Lundquist et al. |
| 5,431,168 A | | 7/1995 | Webster, Jr. |
| 5,464,394 A | | 11/1995 | Miller et al. |
| 5,465,717 A | | 11/1995 | Imran et al. |
| 5,468,233 A | | 11/1995 | Schraga |
| 5,489,270 A | * | 2/1996 | Van Erp ....................... 604/95 |
| 5,498,238 A | | 3/1996 | Shapland et al. |
| 5,514,128 A | | 5/1996 | Hillsman et al. |
| 5,531,685 A | * | 7/1996 | Hemmer et al. .............. 604/95 |
| 5,533,967 A | * | 7/1996 | Imran .......................... 604/95 |
| 5,554,114 A | | 9/1996 | Wallace et al. |
| 5,569,220 A | | 10/1996 | Webster, Jr. |
| 5,571,073 A | | 11/1996 | Castillo |
| 5,571,151 A | | 11/1996 | Gregory |
| 5,607,421 A | | 3/1997 | Jeevanandam ................ 606/15 |
| 5,656,029 A | * | 8/1997 | Imran et al. ............ 604/528 X |
| 5,656,030 A | * | 8/1997 | Hunjan et al. ................ 604/95 |
| 5,662,622 A | | 9/1997 | Gore et al. |
| 5,685,853 A | | 11/1997 | Bonnet |
| 5,697,916 A | | 12/1997 | Schraga |
| 5,741,320 A | * | 4/1998 | Thornton et al. ......... 604/95 X |
| 5,782,824 A | * | 7/1998 | Abela et al. .................. 606/15 |
| 5,827,278 A | | 10/1998 | Webster, Jr. |
| 5,840,059 A | | 11/1998 | March et al. |
| 5,843,076 A | | 12/1998 | Webster, Jr. et al. |
| 5,876,373 A | * | 3/1999 | Giba et al. .................... 604/95 |
| 5,897,529 A | | 4/1999 | Ponzi |
| 5,938,653 A | * | 8/1999 | Pepin .......................... 604/527 |
| 5,944,690 A | * | 8/1999 | Falwell et al. ................ 604/95 |
| 5,964,757 A | | 10/1999 | Ponzi |
| 5,964,971 A | * | 10/1999 | Lunn ............................ 156/86 |
| 5,999,678 A | | 12/1999 | Murphy-Chutorian et al. |
| 6,030,371 A | * | 2/2000 | Pursley ........................ 604/282 |
| 6,165,188 A | * | 12/2000 | Saadat et al. ................ 606/159 |

FOREIGN PATENT DOCUMENTS

| | | |
|---|---|---|
| EP | 0 900 548 A1 | 3/1999 |
| EP | 0 900 549 A1 | 3/1999 |
| EP | 0 900 574 A1 | 3/1999 |
| WO | WO 96/35469 | 11/1996 |
| WO | WO 98/05307 | 2/1998 |

OTHER PUBLICATIONS

"Constitutive Expression of phVEGF 165 After Intramuscular Gene Transfer Promotes Collateral Vessel Development in Patients With Critical Limb Ischemia," Baumgartner, Iris, M.D., et al., The Journal of Thoracic and Cardiovascular Surgery, pvol. 115, No. 1, pp. 1114–1123, Jan. 1998.

"Induction of Neoangiogenesis in Ischemic Myocardium by Human Growth Factors," Schumacher, B., M.D. et al., The Journal of Thoracic and Cardiovascular Surgery, vol. 115, No. 1, Jan. 1998, pp. 645–650.

"Biologic Bypass with the Use of Adenovirus–Mediated Gene Transfer of the Complementary Deoxyribonucleic Acid for Vascular Endothelial Growth Factor 121 Improves Myocardial Perfusion and Function in the Ischemic Porcine Heart,"Mack, Charles A., M.D., The Journal of Thoracic and Cardiovascular Surgery, vol. 115, No. 1, Jan. 1998, pp. 168–177.

"Cardiovascular Applications of Laser Technology," Deckelbaum, Lawrence I., M.D., Lasers in Surgery and Medicine, 15:315–341, 1994.

"Myocardial Revascularization with Laser," Frazier, O.H., et al., Cullen Cardiovascular Research Laboratories, Texas Heart Institute, II–58–II–65, 1995.

Deckelbaum, Lawrence I., M.D., "Cardiovascular Applications of Laser Technology," Lasers in Surgery and Medicine 15:315–341,1994.

Frazier, O.H., M.D. et al.. "Myocardial Revascularization with Laser," Cullen Cardiovascular Research Laboratories, Texas Herat Institute, II–58–II–65, 1995.

* cited by examiner

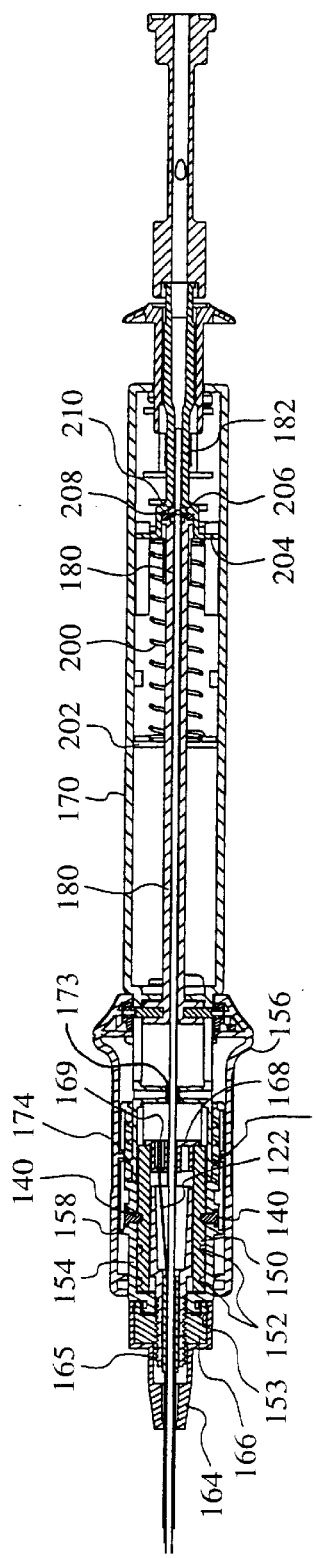
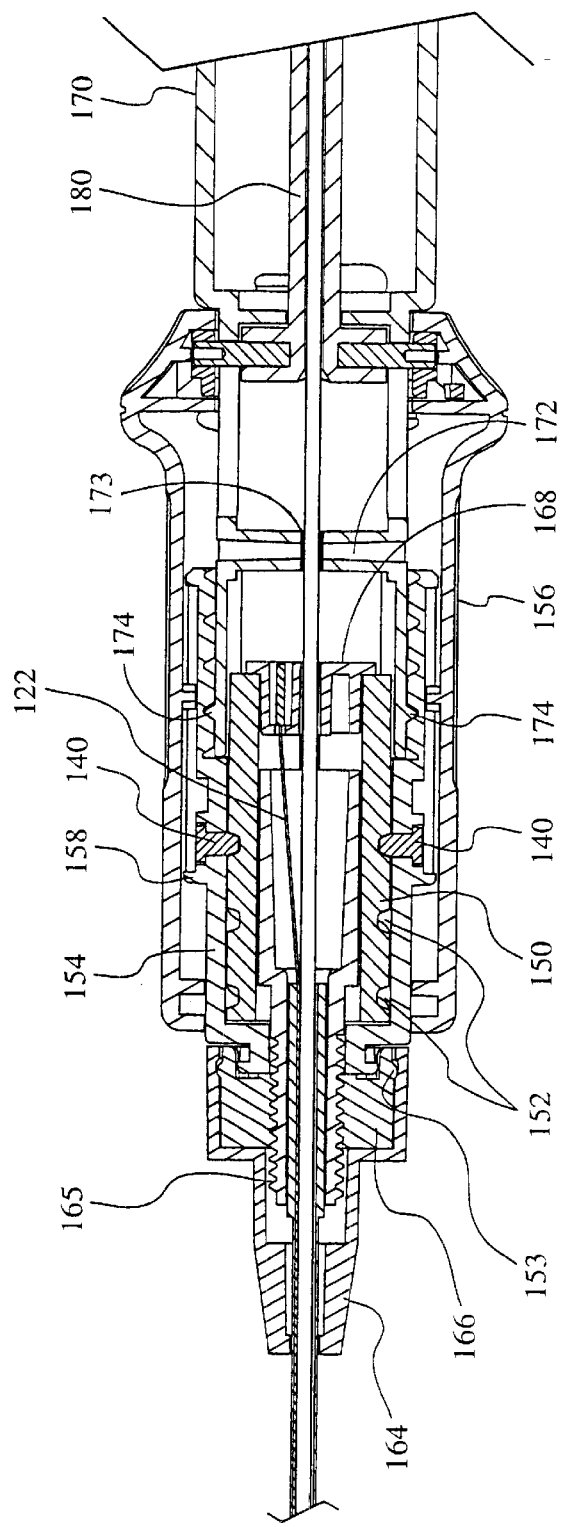
FIG. 3A
FIG. 3AA

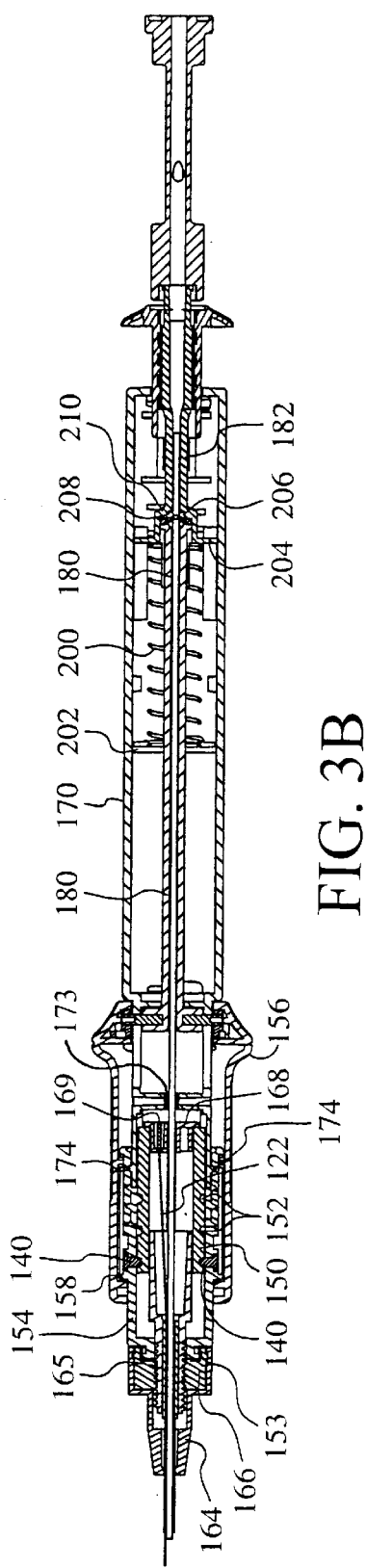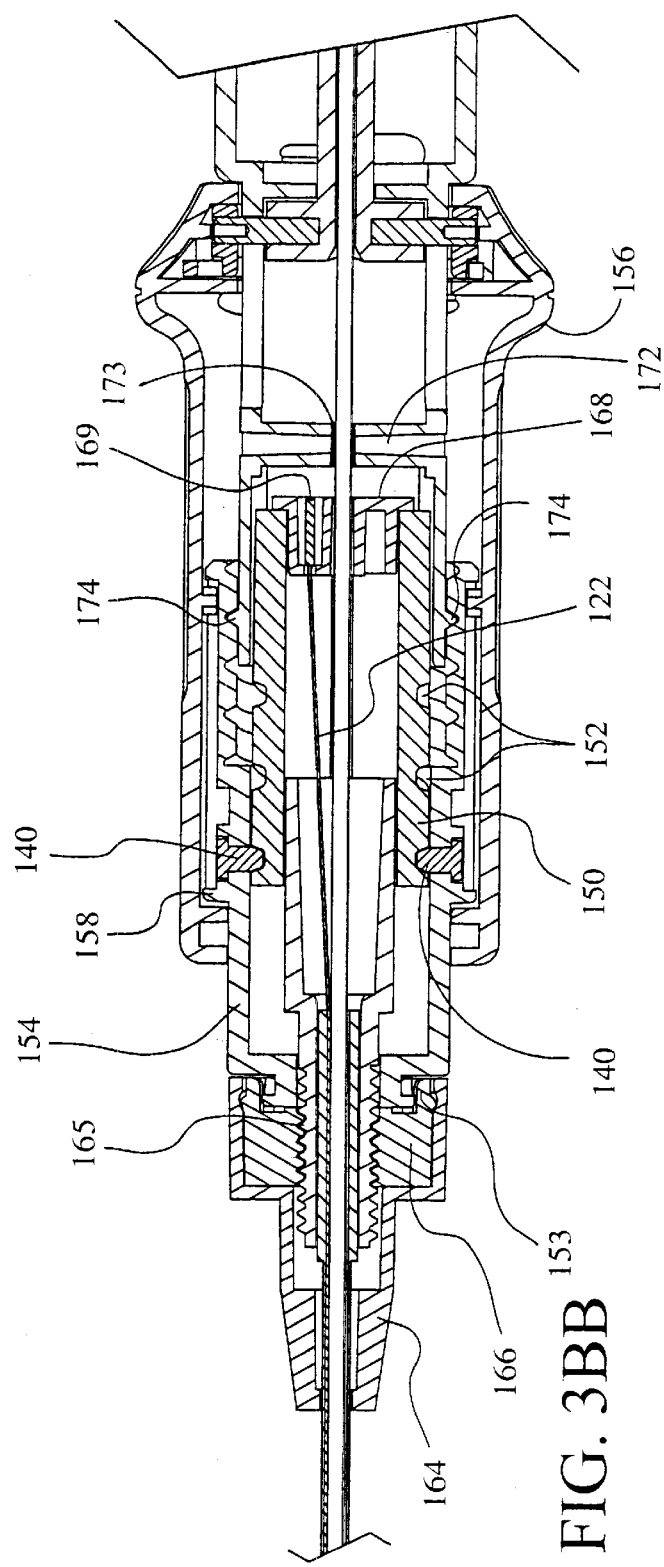
FIG. 3B
FIG. 3BB

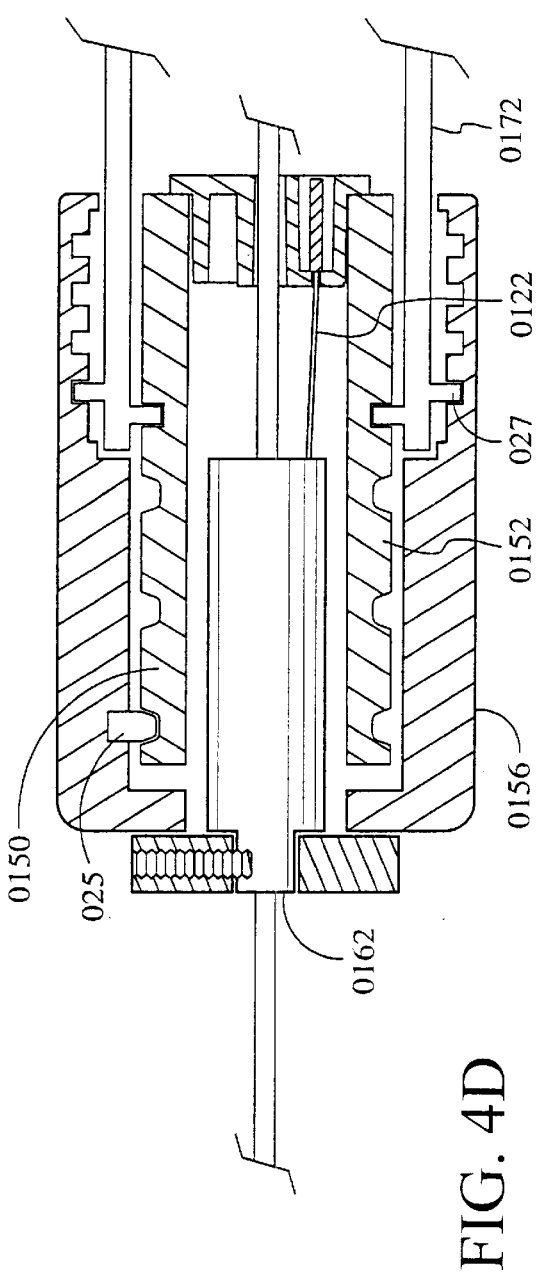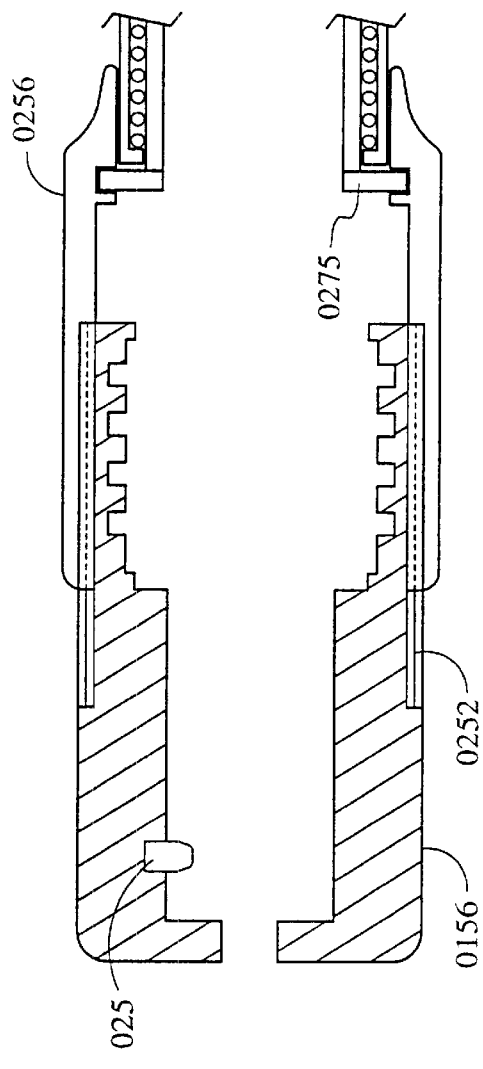
FIG. 4D
FIG. 4E

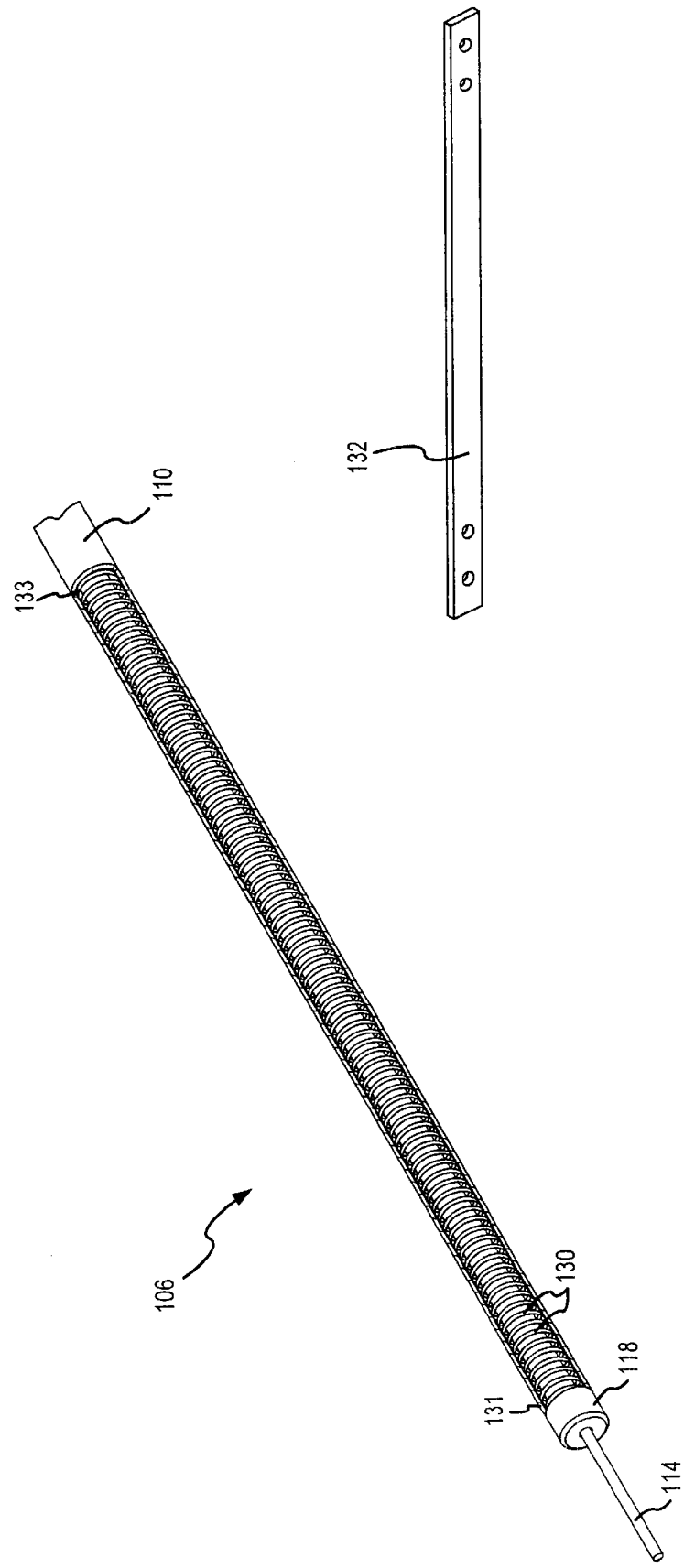

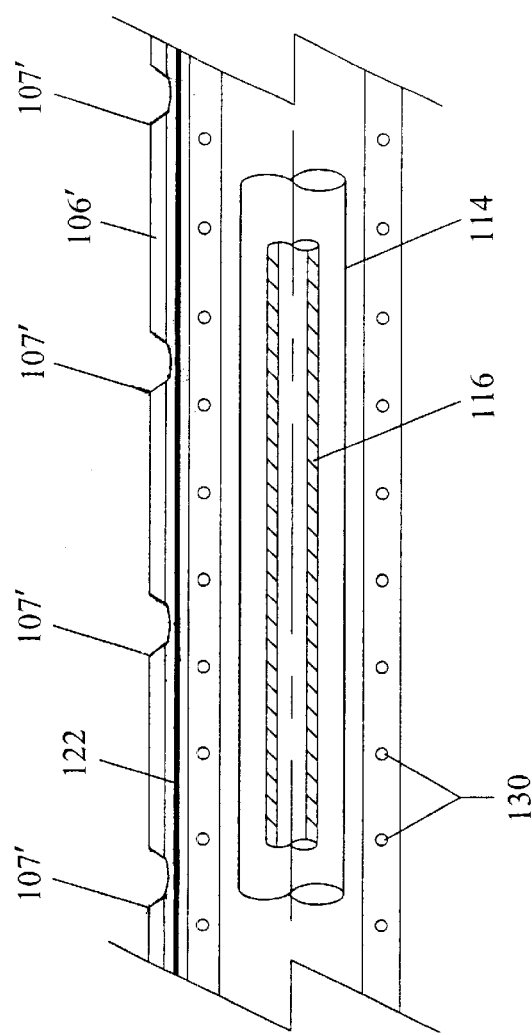
FIG. 8C
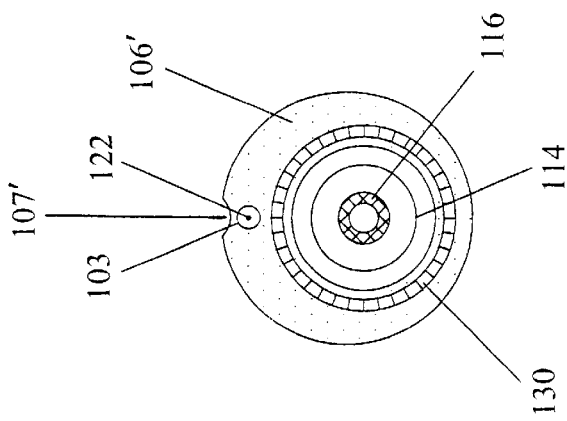
FIG. 8D
107A'  107B'  107C'  107D'
FIG. 8E

NON-DEFORMING DEFLECTABLE MULTI-LUMEN CATHETER

CROSS-REFERENCE TO RELATED APPLICATIONS

This Application is a Continuation-in-Part of application Ser. No. 09/156,963 entitled "STEERABLE CATHETER WITH TIP ALIGNMENT AND SURFACE CONTACT DETECTOR" and application Ser. No. 09/156,964 entitled "DRUG DELIVERY CATHETER WITH TIP ALIGNMENT," now U.S. Pat. No. 6,179,809 both filed Sep. 18, 1998, and of which claim the benefits of domestic priority under 35 U.S.C. Section 119(e) from U.S. Provisional Application Serial No. 60/059,892 entitled "FIBER/CATHETER TIP ALIGNMENT" filed Sep. 24, 1997, and of application Ser. No. 09/080,175 entitled "DRUG DELIVERY MODULE" filed May 16, 1998, now U.S Pat. No. 6,183,444 the specifications, drawings and claims of which are all incorporated herein in their entireties.

FIELD OF INVENTION

The present invention relates generally to non-deforming, deflectable, multi-lumen catheters and catheter procedures involving functional devices, such as laser delivery devices and drug delivery devices. More particularly, the invention relates to a kink-resistant and flexible catheter and method of use, particularly adapted for laser-assisted and/or drug-assisted percutaneous transluminal revascularization (PTMR). The distal tip of the catheter for guiding a laser delivery device, drug delivery device or other functional device extendable there through, is deflectable in at least one given plane. The invention may further an automatic catheter tip alignment system for maintaining constant relative positioning between the distal tip of the functional device and the distal tip of the catheter.

BACKGROUND OF INVENTION

In the treatment of heart disease, one method of improving myocardial blood supply is called transmyocardial revascularization (TMR), the creation of channels in the myocardium of the heart. The procedure using needles in a form of surgical myocardial acupuncture has been used clinically since the 1960s. Deckelbaum. L. I., Cardiovascular Applications of Laser Technology, Lasers in Surgery and Medicine 15:315–341 (1994). The technique relieves ischemia by allowing blood to pass from the ventricle through the channels either directly into other vessels communicating with the channels or into myocardial sinusoids which connect to the myocardial microcirculation.

In the reptilian heart, perfusion occurs via communicating channels between the left ventricle and the coronary arteries. Frazier, O. H., Myocardial Revascularization with Laser—Preliminary Findings, Circulation, 1995; 92 [suppl II]:II-58–II-65. There is evidence of these communicating channels in the developing human embryo. In the human heart, myocardial microanatomy involves the presence of myocardial sinusoids. These sinusoidal communications vary in size and structure, but represent a network of direct arterial-luminal, arterial-arterial, arterial-venous, and venous-luminal connections. This vascular mesh forms an important source of myocardial blood supply in reptiles but its role in humans is poorly understood.

Numerous surgical TMR studies have been performed, including early studies using needles to perform myocardial acupuncture, or boring, to mechanically displace and/or remove tissue. Such studies have involved surgically exposing the heart and sequentially inserting needles to form a number of channels through the epicardium, myocardium, and endocardium to allow blood from the ventricle to perfuse the channels. The early studies using needles showed that the newly created channels were subject to acute thrombosis followed by organization and fibrosis of clots resulting in channel closure. Interest in TMR using needles waned with the knowledge that such channels did not remain open. However, interest in TMR procedures has recurred with the advent of medical lasers used to create TMR channels. Histological evidence of patent, endothelium-lined tracts within laser-created channels shows that the lumen of laser channels can become hemocompatible and resists occlusion. A thin zone of charring occurs on the periphery of the laser-created channels through the well-known thermal effects of optical radiation on cardiovascular tissue. Additionally, recent histological evidence shows probable new vessel formation adjacent collagen occluded transmyocardial channels, thereby suggesting benefits from TMR with or without the formation of channels which remain patent.

Surgical TMR procedures using laser energy have been described. U.S. Pat. No. 4,658,817 issued Apr. 21, 1987 to Hardy teaches a method and apparatus for surgical TMR using a $CO_2$ laser connected to an articulated arm having a hand piece attached thereto. The hand piece emits laser energy from a single aperture and is moved around the surface of the heart to create the desired number of channels. U.S. Pat. No. 5,380,316 issued Jan. 10, 1995 to Aita et al. purports to teach the use of a flexible lasing apparatus which is inserted into the open chest cavity in a surgical procedure. A lens at the distal end of the flexible apparatus is used to focus laser energy, and the apparatus is moved about the surface of the heart to create the desired number of channels.

The foregoing discussion relates to surgical procedures, i.e. procedures which access the heart surgically, either via open heart surgery, or perhaps by minimally invasive surgical (MIS) methods if the design and size of the distal ends of the hand pieces are suitable for use in an MIS site. However, since TMR most often involves creating channels through the epicardium into the lower left chamber of the heart, it is desirable to create TMR channels in a percutaneous procedure, i.e. by extending a catheter apparatus through the vasculature into the ventricle and creating the channels through endocardial surfaces and into myocardium. Performing percutaneous TMR (PTMR) is desirable for a number of reasons. Percutaneous catheter procedures are typically less traumatic to the patient compared to surgical procedures. Adhesions between the pericardial sac and epicardium are eliminated. Percutaneous TMR with a catheter apparatus also offers an alternative solution to persons who are not candidates for surgical procedures.

Because TMR procedures generally involve creating a plurality of channels within the myocardium, performing the procedure percutaneously requires the ability to steer a catheter apparatus through the vasculature and maneuver the apparatus within the ventricle of the beating heart as rapidly as possible to create the channels without subjecting the heart to the undue stress of a lengthy procedure. Additionally, the ability to control and stabilize the catheter apparatus against the beating heart wall while creating channels with a laser is desirable for percutaneous procedures to ensure creation of channels as desired and to ensure that the laser is fired only within the myocardial tissue. TMR channels should be spaced and grouped appropriately to achieve the desired result without weakening or rupturing the heart muscle.

The early myocardial acupuncture procedures were not performed percutaneously. The Hardy $CO_2$ laser delivery system described above is rigid, relatively large, and not adaptable for percutaneous use. The Aita '316 patent does not suggest a method for percutaneous use of the laser delivery device described therein for surgical use.

U.S. Pat. No. 5,389,096 issued Feb. 14, 1995 to Aita et al. purports to teach one method of percutaneous TMR using an elongated flexible lasing apparatus with control lines and a focusing lens structure at the distal tip. The method uses pressure applied manually to attempt to stabilize the apparatus against the wall of the heart.

Several patents describe the use of catheters within the ventricle for percutaneous treatment of ventricular tachycardia. Such devices have a means to locate an arrhythmia site and ablate the site, at or just below the ventricle surface, using an electrode device or laser energy. U.S. Pat. No. 5,104,393 issued Apr. 14, 1992 to Isner teaches a catheter apparatus having a guiding Y-shaped sheath and guide catheter assembly for introducing an optical fiber into the ventricle. Positioning is described to enable a single burst of laser energy from a single aperture to ablate the site.

U.S. Pat. No. 5,190,050 issued Mar. 2, 1993 to Nitzsche teaches a steerable catheter with a handle and a tube, the distal tip of which may be selectively curved by controllably moving one of three flat, sandwiched shims relative to the others by manipulation of a handle portion.

U.S. Pat. No. 5,358,479 issued Oct. 25, 1994 to Wilson, incorporated herein in its entirety by reference, teaches another steerable catheter with a handle and an inner tube, the apparatus having a single elongated, substantially flat shim spring mounted within the tip of the catheter tube, the shim having at least one transverse or lateral twist which causes the tip of the catheter tube to assume a desired curvature.

Drug therapies with angiogenic growth factors may expedite and/or augment collateral artery development. "Biologic Bypass with the Use of Adenovirus-Mediated Gene Transfer of the Complementary Deoxyribonucleic Acid for Vascular Endothelial Growth Factor 121 Improves Myocardial Perfusion and Function in the Ischemic Porcine Heart," by Mack et al., The J. of Thorac. and Cardiovascular Surgery, Vol. 115, No. 1, January 1998, p. 168–177, delivery of vascular endothelial growth factor (VEGF) can be delivered to targeted tissues, by means of a replication deficient adenovirus (Ad) vector, to induce collateral vessel development in ischemic myocardium for improvement of both myocardial perfusion and function. "Introduction of Neoangiogenesis in Ischemic Myocardium by Human Growth Factors", by B. Schumacher et al, The J. of Thorac. and Cardiovascular Surgery, Vol. 115, No. 1, January 1998, p. 645–650, teaches the use of FGF-1, a growth factor produced using recombinant-DNA technology, for the treatment of coronary heart disease based upon development of new vessels and the formation of capillaries in areas of stenoses. "Constitutive Expression of phVEGF after Intramuscular Gene Transfer Promotes Collateral Vessel Development in Patients with Critical limb Ischemia," Baumgartner et al., The J. of Thorac. and Cardiovascular Surgery, Vol. 115, No. 1, January 1998, p. 1114–1123, teaches intramuscular injection of naked plasmid DNA encoding an endothelial cell mitogen to cause formation of collateral blood vessels, improved distal flow in many limbs, including healing of ulcers and successful limb salvage.

U.S. Pat. No. 5,409,453 issued Apr. 25, 1995 to Lundquist et al. teaches a steerable medical probe with stylets. The device is designed for reducing the mass of a body part, such as for biopsy sampling or for removing prostatic tissue in the case of BPH. The torquable catheter has a control end and a probe end, the probe end having a stylet guide means with a flexible tip and a tip directing means extending from the control end to the flexible tip for changing the orientation of the central axis of the stylet guide means for directing a flexible stylet outward through the stylet port and through intervening tissue to targeted tissues.

U.S. Pat. No. 5,571,151 issued Nov. 5, 1996 to Gregory teaches a method for contemporaneous application of laser energy and localized pharmacologic therapy. The method comprises preparing a solution of a pharmacologic agent, inserting the catheter into the lumen, directing the catheter to the site, transmitting visible light to the site, flowing the light transmissive liquid through the catheter, viewing the site, transmitting laser energy through the liquid filled catheter to treat the site, and introducing a flow of the pharmacologic agent in solution into the catheter for contemporaneous discharge at the distal end into the lumen adjacent the site.

The use of superelastic and/or shape memory materials is widely known. *Structure and Properties of Ti—NI Alloys: Nitinol Devices & Components,* Duerig et al., In Press, Titanium Handbook, ASM (1994) In general, binary compositions of Nickel (Ni) and Titanium (Ti), yield alloys with shape memory and superelastic properties. These alloys are commonly referred to as Ni—Ti, nitinol, and other industry names. Their precise physical and other properties of interest are extremely sensitive to the precise Ni/Ti ratio used. Generally, alloys with 49.0 to 50.7 atomic % of Ti are commercially available, with superelastic alloys in the range of 49.0 to 49.4%, and shape memory alloys in the range of 49.7 to 50.7%. Due to a rapid decrease in the ductility of the material, binary alloys with less than 49.4 at % Ti are generally unstable. In general, these types of materials exhibit hysteresis, defined as a phenomenon exhibited by a system whose state depends on its previous history, and illustrated diagrammatically by the familiar upper and lower curves which meet at the ends and define an area under the curves. In the case of solid materials undergoing elastic hysteresis (as opposed to magnetic or electrical hysteresis), the curves are related to stress necessary to cause deformation or otherwise overcome existing stress in pre-stressed materials.

For the purposes of this disclosure, a distinction between superelastic materials and shape memory materials is made. Superelasticity refers to the highly exaggerated elasticity, or springback, observed in many Ni—Ti alloys deformed at a specific temperature. The function of the material in many of such cases is to store mechanical energy. Though limited to a rather small temperature range, these alloys can deliver over 15 times the elastic motion of a spring steel, i.e., withstand a force up to 15 times greater without permanent deformation. Shape memory materials will refer to those materials which can be deformed, but which will freely recover their original shapes during heating, often utilizing electrical resistivity, or which will develop a large recovery stress when recovery is prevented. With regard to the present invention, it will be understood that the transition temperature of materials must, in general, be somewhat above body temperature.

U.S. Pat. No. 3,890,977 issued Jun. 24, 1975 to Wilson teaches kinetic memory electrodes, catheters and cannulae. These devices incorporate a material, such as a Ni—Ti alloy, having heat-activated mechanical memory properties. The device is formed into an operative shape at a high temperature. Then, at a low temperature below its transitional temperature, it is reformed into a shape for ease of insertion into a guide catheter or the like or otherwise through a portion of a patients vasculature or other body lumen. When located in the organ or other desired region, those portions of the device constructed using such shape memory materials are heated to above their transitional temperatures, using electrically resistive elements, thereby returning the catheter to its original annealed anchoring or proper locating shape. An important drawback of the Wilson apparatus is that heat must be applied to the catheter tip. Complicated construction and electrical power distribution must be considered.

U.S. Pat. No. 5,114,402 issued May 19, 1992 to McCoy teaches a maneuverable distal apparatus with a temperature activated material of construction which, upon heating to a predetermined position, will assume a predetermined, memorized shape, and which upon cooling, will assume a different shape by action of a spring element urging the apparatus into the different shape.

U.S. Pat. No. 4,920,980 issued May 1, 1990 to Jackowski teaches a catheter with controllable tip. A wire member is loosely positioned inside a central bore of the catheter so that the distal tip of the catheter can be bent by pulling the wire member.

U.S. Pat. No. 5,279,596 issued Jan. 18, 1994 to Castaneda et al. teaches an intravascular catheter with kink resistant tip. The catheter has a construction utilizing proximal and distal components with varying degrees of stiffness or durometer. Additionally, the distal tip has a helical wire support member embedded therein, for providing kink resistance to the distal portion upon bending thereof.

U.S. Pat. No. 4,960,134 issued Oct. 2, 1990 and U.S. Pat. No. Re. 34,502 issued Jan. 11, 1994, both to Webster, Jr., teach a steerable catheter having a control handle with piston mounted therein and a puller wire extending from the housing of the handle, through the piston and through and coaxial with the catheter body. The puller wire extends into an offset lumen of the catheter tip wherein it is attached to the wall of the catheter tip, such that lengthwise movement of the piston relative to the housing results in deflection of the catheter tip.

U.S. Pat. No. 5,431,168 issued Jul. 11, 1995 to Webster, Jr. teaches a steerable open-lumen catheter. A first lumen which extends the entire length of the catheter is open at the distal end of the catheter. A second, off-set lumen contains a tightly wound coil spring with a puller wire slidably disposed within the coil spring. Manipulation of a handle portion results in deflection of the tip portion without deflection of the catheter portion.

A common mode of failure of steerable catheters of the prior art is that upon positioning and retraction of the pull wire or pull cable, the distal end of the catheter may deform and develop an "S" shape. The problem, as described, is often due to inadequately supported distal end of the catheter. This may prevent deflection of the distal tip in some cases. In other catheters, including drug delivery catheters, pinching of the outer jacket around an internally restricted drug delivery tube seals the saline lumen caused during bending of the assembly, which restricts advancing or retracting movement of the delivery tube within the saline lumen, and prevents flow of fluids either way through the saline lumen.

There is a need for deflectable percutaneous catheters, especially PTMR steerable catheters, which automatically maintain alignment of the distal end of the catheter with the distal end of a functional device therein during catheter deflection movement relative to an interior body surface, particularly a ventricular wall. There is also a need for catheters which are deflectable yet which resist kinking or distortion, thereby preventing advancement or retraction of the functional device therein or otherwise restricting proper use thereof. Additionally, it would be desirable to provide such a non-deformable, deflectable catheter with an optional automatic compensation mechanism for alignment of inner and outer portions of the system during deflection and use.

ADVANTAGES AND SUMMARY OF INVENTION

Thus, it is an advantage of the present invention to provide a non-deformable, deflectable catheter and method of use for percutaneous and other intra-vascular procedures, including but not limited to PTMR, or any stimulation procedure. The deflectable distal portion of the catheter resistant to kinking or other undesirable distortion during deflection and use thereof.

It is a further advantage of the present invention to provide a non-deforming catheter having a deflection and translation mechanism, a hollow outer jacket having a deflectable distal portion and an at least partially embedded pull wire lumen and coupled at a proximal end to the deflection and translation mechanism, a tip coupled to a distal end of the outer jacket, an inner tube with lumen in the hollow of the outer jacket, at least one functional device disposed in the lumen having a distal end extendable from the tip of the catheter and a pull wire contained in the pull wire lumen having a distal end coupled to the tip and a proximal end coupled to the deflection mechanism, the pull wire effecting non-deforming deflection of the deflectable distal portion of the outer jacket and functional device therein by movement of the deflection mechanism.

It is a further advantage of the present invention to provide a non-deformable deflectable catheter wherein the deflectable portion bends up to about 270 degrees.

It is a further advantage of the present invention to provide a non-deformable deflectable catheter with a coil embedded in the deflectable portion of the outer jacket.

It is a further advantage of the present invention to provide a non-deformable deflectable catheter with an at least partially embedded shim in the deflectable portion of the outer jacket.

It is a further advantage of the present invention to provide a non-deformable deflectable catheter with a coil embedded and an at least partially embedded shim in the deflectable portion of the outer jacket.

It is a further advantage of the present invention to provide a non-deformable deflectable catheter with one or more notches in an outer surface of the outer jacket and aligned with the pull wire.

It is a further advantage of the present invention to provide a non-deformable deflectable catheter with one or more notches in an outer surface of the outer jacket, aligned with the pull wire, and a coil embedded in the deflectable portion of the outer jacket.

It is a further advantage of the present invention to provide a non-deformable deflectable catheter in which the pull wire lumen has a proximal end embedded in the inner tube and a distal end at least partially embedded in the deflectable distal portion of the outer jacket.

It is a further advantage of the present invention to provide a non-deformable deflectable catheter with a relative movement compensation mechanism for maintaining alignment between the outer jacket and the functional device coupled to the deflection mechanism whereby movement of the deflection mechanism causes simultaneous movement of the relative movement compensation mechanism.

It is a further advantage of the present invention to provide a non-deformable deflectable catheter wherein the outer jacket is comprised of one or more polymers having one or more flexibility.

It is a further advantage of the present invention to provide a non-deformable deflectable catheter wherein the proximal end of the outer jacket further comprises a braided construction.

It is a further advantage of the present invention to provide a non-deformable deflectable catheter wherein a distal portion of the apparatus comprises one or more radio opaque materials.

It is a further advantage of the present invention to provide a non-deformable deflectable catheter wherein the functional device is an energy delivery device, such as a laser energy delivery device, optionally in combination with a drug delivery device, or a drug delivery tube with a piercing needle distal end.

It is a further advantage of the present invention to provide a non-deformable deflectable catheter wherein the translation mechanism is coupled to a drug delivery module, the functional device is a drug delivery tube with a piercing needle coupled to a distal end and further comprising a relative movement compensation mechanism for maintaining alignment between the outer jacket and the drug delivery tube coupled to the deflection mechanism whereby movement of the deflection mechanism causes simultaneous movement of the movement compensation mechanism.

It is a further advantage of the present invention to provide a non-deforming catheter apparatus for delivering drugs to the myocardium having a deflection mechanism, a drug delivery module coupled to the mechanism, a hollow outer jacket having a deflectable distal portion with an embedded coil and shim, each having a proximal end coupled to the deflection mechanism, a tip coupled to a distal end of the outer jacket, an inner tube with lumen in the hollow of the outer jacket, a pull wire lumen having a proximal end embedded in the inner tube and a distal end at least partially embedded in the deflectable distal portion of the outer jacket, a drug delivery tube disposed in the lumen and having a distal end with a piercing needle, a distal tip of the piercing needle extendable from the tip of the catheter, and a pull wire contained in the pull wire lumen and having a distal end coupled to the tip and a proximal end coupled to the deflection mechanism, whereby the pull wire effects non-deforming deflection of the deflectable distal portion of the outer jacket and drug delivery tube therein by movement of the deflection mechanism. It is yet a further advantage to have a relative movement compensation mechanism for maintaining alignment between the outer jacket and drug delivery tube when the deflectable distal portion is deflected, in combination with the deflection mechanism of the non-deforming drug delivery apparatus.

A further advantage of the present invention is to provide a non-deforming catheter apparatus for performing percutaneous transluminal myocardial revascularization comprising a deflection and relative movement compensation mechanism, a hollow outer jacket having a deflectable distal portion with an embedded coil and shim coupled at a proximal end to the deflection and relative movement compensation mechanism, a tip coupled to a distal end of the outer jacket, an inner tube with lumen in the hollow of the outer jacket, a laser energy delivery device disposed in the lumen having a distal end extendable from the tip of the catheter, a pull wire lumen having a proximal end embedded in the inner tube and a distal end at least partially embedded in the deflectable distal portion of the outer jacket; and a pull wire contained in the pull wire lumen having a distal end coupled to the tip and a proximal end coupled to the deflection and relative movement compensation mechanism, whereby the relative movement compensation mechanism maintains alignment between the outer jacket and laser energy delivery device when the pull wire effects non-deforming deflection of the deflectable distal portion of the outer jacket and laser energy delivery device therein by movement of the deflection mechanism.

Numerous other advantages and features of the present invention will become readily apparent from the following detailed description of the invention and the embodiments thereof, from the claims and from the accompanying drawings.

BRIEF DESCRIPTION OF THE DRAWINGS

FIG. 3A is a representative sectional view of the proximal portion of the nondeforming deflectable catheter of the present invention using a rotatable differential screw mechanism with an integrated functional device advance mechanism for achieving autoalignment of the distal tip of the catheter and functional device in an undeflected position.

FIG. 3AA is an enlarged view of detail 3A.

FIG. 3B is a representative section view of the proximal portion of the nondeforming deflectable catheter of the present invention using a rotatable differential screw mechanism with an integrated functional device advance mechanism for achieving autoalignment of the distal tip of the catheter and functional device in a deflected position.

FIG. 3BB is an enlarged view of detail 3B.

FIG. 4D is a partial cut-away view of an embodiment of the handle using a rotatable differential screw mechanism showing functional device or fiber advance and deflection components for achieving auto-alignment of the tip of the functional device or fiber optical tip.

FIG. 4E is a cross-sectional view of a variation of the embodiment of the handle device using an integrated rotatable differential screw with an integrated fiber advance mechanism for achieving auto-alignment of the optical fiber tip.

FIG. 7AA is a representative isometric view of the deflectable distal end portion of the embodiment of the catheter with coil as shown in FIG. 7.

FIG. 7AAA is a representative isometric view of the shim as shown in FIG. 7A and 7B.

FIG. 7BB is a representative isometric detail view of the assembly of the deflectable distal end portion of the embodiment of catheter shown in FIG. 7B.

FIG. 7CC is another representative isometric detail view of the assembly of the deflectable distal end portion of the embodiment of the catheter shown in FIG.7.

FIG. 8C is a representative lengthwise cross section view of an alternate embodiment of the deflectable distal end portion of the non-deforming deflectable catheter of the present invention with an embedded coil and notches and without a shim.

FIG. 8D is a representative perpendicular cross section view of the alternate embodiment shown in FIG. 8C.

FIG. 8E is a selection of possible and representative cross section profiles of notches for use with the alternate embodiment of the catheter as shown in FIG. 8C.

DETAILED DESCRIPTION

Figure 1:
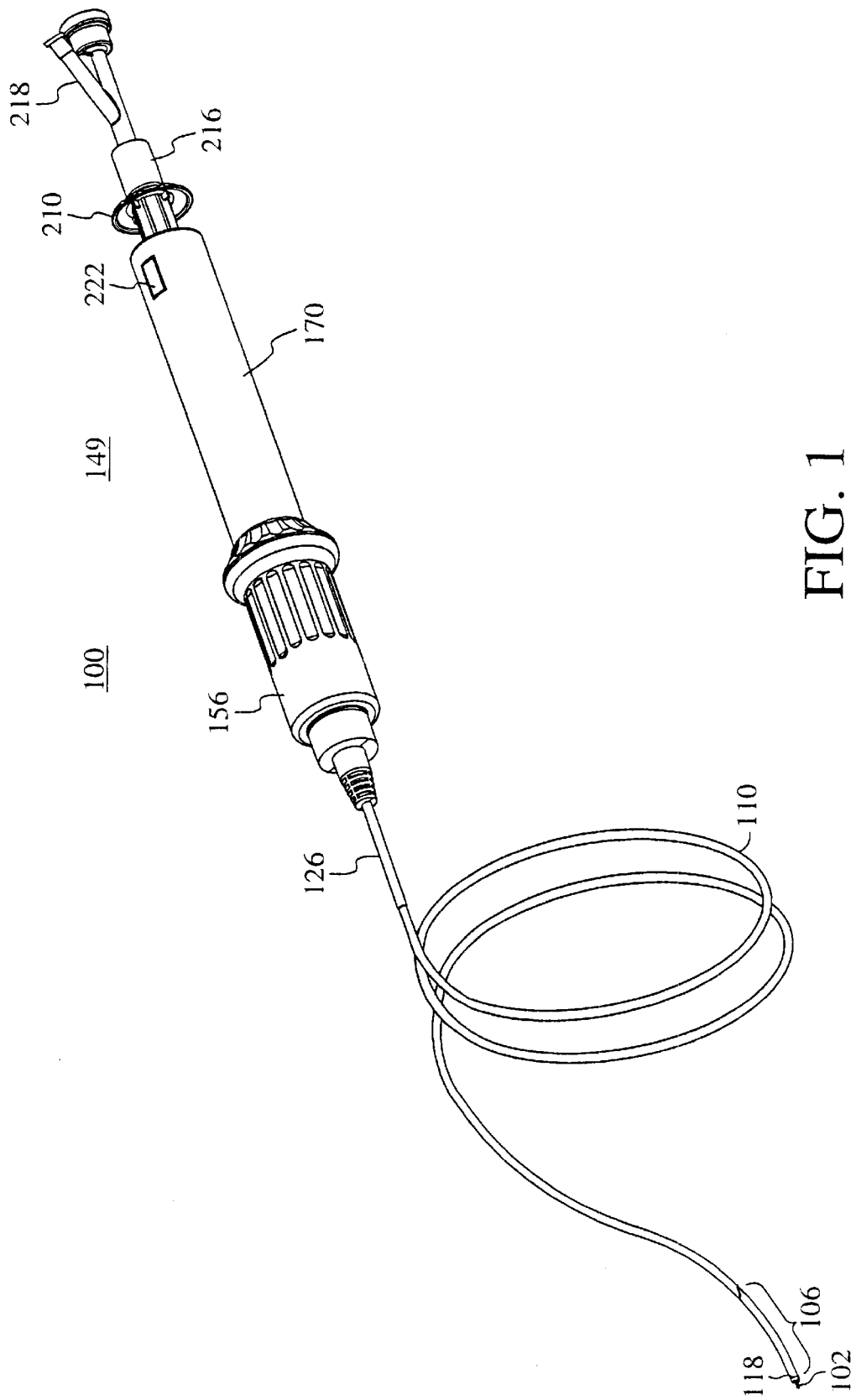
FIG. 1 is a representative isometric view of the preferred embodiment of the non-deforming deflectable multi lumen catheter with auto-alignment of the present invention.

FIG. 1 is a representative isometric view of the preferred embodiment of the non-deforming, deflectable, multi lumen catheter 100 with optional auto-alignment of the present invention. The catheter 100 has a handle 170 and an actuator 156 at its proximal portion 149 and a non-deforming controllably deflectable distal portion 106 of an elongated catheter or outer jacket 110. The deflectable end portion 106 is more flexible than the rest of the elongated catheter 110, allowing the deflectable end portion 106 to develop a controlled bend with a small radius of curvature. Components for effecting multiple degrees of freedom of the distal tip of the catheter as well as other features for steerable catheter systems are disclosed in U.S. Pat. No. 5,876,373, entitled STEERABLE CATHETER by Giba et al. filed Apr. 4, 1997 and issued Mar. 2, 1999, which is hereby incorporated by reference in its entirety. The deflectable end portion of the catheter or outer jacket 106, as well as the catheter or outer jacket 110, may be formed having variable degrees of flexibility or stiffness throughout the assembly of the catheter 100. Embodiments can be formed of extrusions having regions of increasing flexibility and/or decreasing flexibility. The more rigid sections may have one or more layers of different materials, including woven or braided layers, including materials such as fiberglass, PEBAX™ (block copolymer amide) or similar, or other types of nylon, stainless steel, chemical or high temperature setting or any other polymers and extrudable materials, etc. An interventional or other functional device translates linearly within the catheter and the distal tip of the functional device, 102, is egressible from the distal tip of the catheter 118, as shown. The functional device may be an energy delivery device, such as a laser, ultrasound or radio frequency energy delivery device, particularly an optical fiber or optical fiber bundle, or a drug delivery tube or mechanical tool.

Figure 1A:
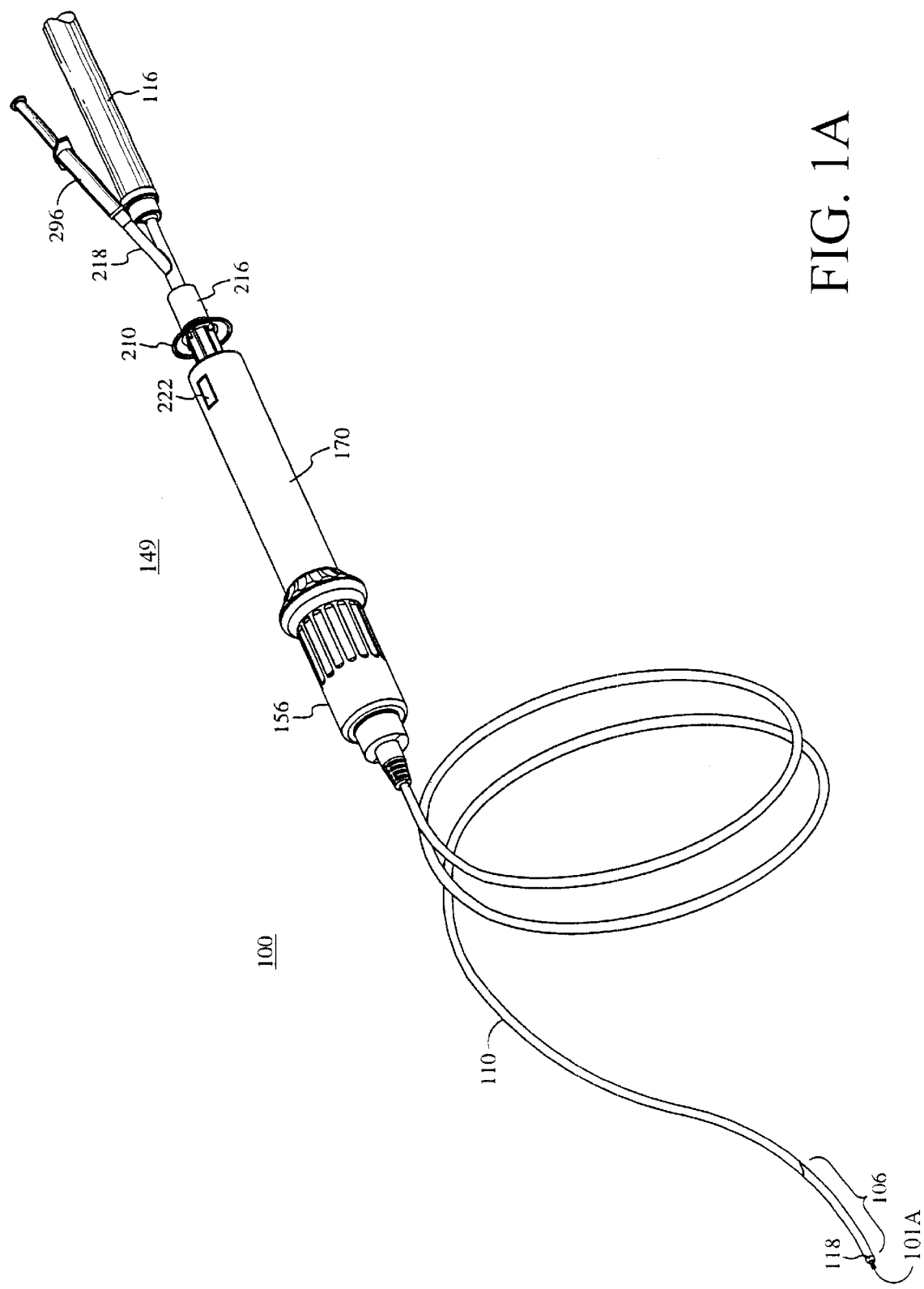
FIG. 1A is a representative isometric view of the preferred embodiment of the non-deformable deflectable catheter of the present invention with a drug delivery apparatus coupled to the proximal end.

FIG. 1A is a representative isometric view of the non-deformable deflectable catheter of the present invention with a drug delivery apparatus 296 coupled to the proximal portion 149 with the distal tip of the functional device, as shown drug delivery needle 101A, extending beyond the distal end of the catheter 100. Drug delivery or dispensing apparatus 296 can be manually or automatically activated, can be adjustable or programmable to dispense individual aliquots of a predetermined volume, at a predetermined or specified rate, as desired.

Figure 2:
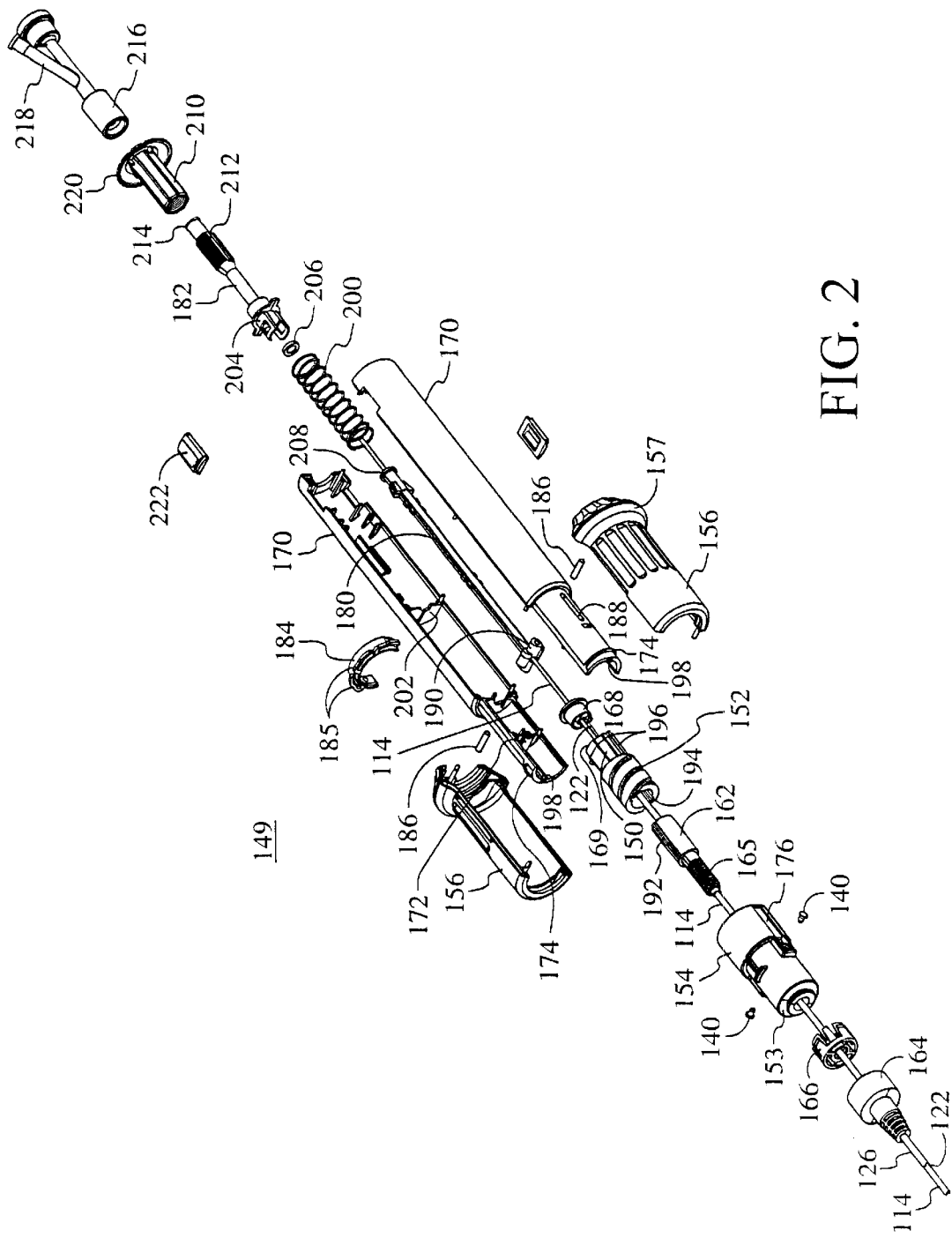
FIG. 2 is a representative exploded view of the internal assembly of the proximal portion of the non-deforming, deflectable catheter of the present invention using a rotatable differential screw mechanism with an integrated functional device advance mechanism for achieving auto-alignment of the distal tip of the catheter and functional device.

FIG. 2 is a representative exploded view of the internal assembly of the proximal portion 149 of the non-deforming deflectable catheter 100 of the present invention using a rotatable differential screw mechanism with an integrated functional device advance mechanism for achieving autoalignment of the distal tip of the catheter and functional device described in detail in U.S. patent applications Ser. Nos. 09/156,193 and 09/156,964 entitled STEERABLE CATHETER WITH TIP ALIGNMENT AND SURFACE CONTACT DETECTOR and DRUG DELIVERY CATHETER WITH TIP ALIGNMENT respectively.

FIGS. 3A and 3B are representative sectional views of the proximal portion of the non-deforming deflectable catheter (shown in FIG. 2) using a rotatable differential screw mechanism with an integrated functional device advance mechanism for achieving autoalignment of the distal tip of the catheter and functional device in an undeflected and deflected position, respectively. FIGS. 3AA and 3BB are enlarged views of FIGS. 3A and 3B respectively.

As seen in FIGS. 2–3BB, outer catheter jacket 110 terminates at its proximal end 126 and is coupled to catheter base 162. Proximal hub 166 is contained within the catheter boot 164 and threads over inside stepped and threaded portion 165 of catheter base 162. The proximal hub 166 is coupled to a distal flange portion 153 of inner deflection knob 154. Deflection actuator 150 slides over catheter base 162 and has an external helical grooved portion 152 located distally on the deflection actuator 150. Two pins 140 attached to inner deflection knob 154 engage helical groove 152, thus rotation of inner deflection knob 154 about deflection actuator 150 translates into linear motion between inner deflection knob 154 and deflection actuator 150. An actuator 156 (shown in two sections in FIG. 2) couples radially around the inner deflection knob 154 and translates linearly with respect to inner deflection knob 154. The actuator 156 engages inner deflection knob 154 at flange 158.

The catheter of the present invention is preferably used with the auto-alignment mechanism, wherein the inner tube 114 is attached to handle 170 at coupling point 173. However in an alternate embodiment it may be used without the auto-alignment mode, wherein the inner tube 114 is free to slide within handle 170 during deflection and is not bonded but only guided by point 173. In the auto-alignment mode, a distal external, helical rib or thread 174 on the handle 170 fits into and acts in cooperation with an operatively pitched and contoured internal helical slot or groove 176 located proximally on the inner deflection knob 154. The inner tube 114 continues proximally, sliding through a front tube 180 and terminates within a back tube 182. A bushing 184 is mounted on bushing pins 186 which extend through longitudinal slots 188 located distally within handle 170 and extend into pin seats 190 located distally on front tube 180. Thus, as the front tube 180 is moved linearly with respect to the handle 170, the bushing pins 186 move linearly within slots 188.

Relative motion between the front tube 180 and the handle 170 is limited to linear motion; there is no rotational motion between the front tube 180 and the handle 170 as such is prevented by the bushing pins 186 which only slide linearly in slots 188. Similarly, axially and longitudinally extending ribs or keys 192 located proximally and externally on catheter base 162 slide linearly within correspondingly shaped linear grooves 194 located internally and distally on deflection actuator 150 opposite the external helical groove 152, thus preventing rotational motion as between the catheter base 162 and the deflection actuator 150. Finally, axially and longitudinally extending ribs or keys 196 located proximally and externally on deflection actuator 150 slide linearly within correspondingly shaped linear grooves 198 located internally and distally on handle 170 at a point distal to slots 188, thus preventing rotational motion as between the deflection actuator 150 and the handle 170.

Pull wire 122 extends proximally from the catheter tip 118 through the catheter base 162 and through the deflection actuator 150, and terminates at pull wire stop 168. Pull wire 122 biases pull wire stop 168 against the proximal end 169 of deflection actuator 150.

The actuator 156 rotates around the bushing 184 and the entire assembly including the actuator 156, the bushing 184, bushing pins 186 seated in the front tube 180 along with the front tube 180, back tube 182 and proximal assembly all translate linearly. Additionally, as the actuator 156 is rotated about a central axis, the inner deflection knob 154 is co-operatively and simultaneously similarly rotated thus effectuating linear translation of deflection actuator 150 and thereby increasing tension in pull wire 122. To prevent the contractive forces on the pull wire 122 which deflect the catheter 100 and translate into counter-rotational forces on the actuator 156 from actually causing the assembly to essentially "unwind", therefore, bushing 184 is constructed with several detents 185 which compress between actuator 156 and handle 170 distally. In a preferred embodiment of the bushing 184, therefore, the resilient detents 185 are distributed around the bushing 184 so as to engage one or more correspondingly shaped grooves, indentations within the proximal flange 157 on actuator 156.

Therefore, as the actuator 156 is rotated in a first direction so as to cause deflection of the deflectable portion 106 of the catheter 100, engagement of the detents 185 of the bushing 184 within the proximal flange 157 of the actuator 156 provides an indexed mechanism, which allows a tactile response by the physician so as to control or at least be aware of the degree of deflection caused by said rotation of the actuator 156. Furthermore, engagement of the detents 185 of the bushing 184 within the proximal flange 157 of the actuator 156 prevents uncontrolled counter-rotation caused by the above described contractive forces developed in the pull wire 122 of the deflected catheter 100. Upon intentional counter-rotation by the physician, resilient detents 185 deform and allow rotation of the actuator 156 as desired. Thus, bushing 184 is designed with resilient detents 185 which provide directionality, i.e., they provide a certain degree of resistant to rotational forces on the actuator 156 intended to deflect the catheter 100 but provide an increased resistance to counter-rotational forces, thereby providing an indexed mechanism with tactile response upon rotation in either direction.

The handle 170 retains a portion of the back tube 182, the back tube 182 slidable through the handle 170 and biased proximally by spring member 200; the spring member 200 is retained between standing rib member 202 extending internally from handle 170 and distal flange 204 on back tube 182. A sealing member 206 is placed between a proximal flange 208 on the front tube 180 and the distal flange 204 on the back tube 182. A depth stop 210 is threaded onto external helical threads 212 of back tube 182 extending proximally from handle 170. A Luer fitting 214 or other suitable coupling and sealing device is useful for coupling a Touhy-Borst type fitting 216 to the back tube 182. An optical fiber, fiber bundle, laser energy delivery device or other energy delivery devices or other functional device may be coupled securely to the Touhy-Borst type fitting 216 and be advanced through the back tube 182 and into the inner tube 114. A saline flush, drug solution, visualization or other therapeutic agent containing fluid can be provided to the catheter via one branched arm 218 of fitting 216 as shown in FIG. 1A. In a preferred embodiment, it will be understood that any back-flow preventer, check valve, blood seal, etc. with the necessary operative function and suitability can be employed elsewhere on the catheter 100 and will be included within the scope of the present invention.

During a PTMR procedure using a catheter as shown in FIG. 1, maintaining alignment between the tip of the fiber 128, or other functional device, and catheter tip 118 is preferred for controlling channel depth in a heart wall.

Figure 4A:
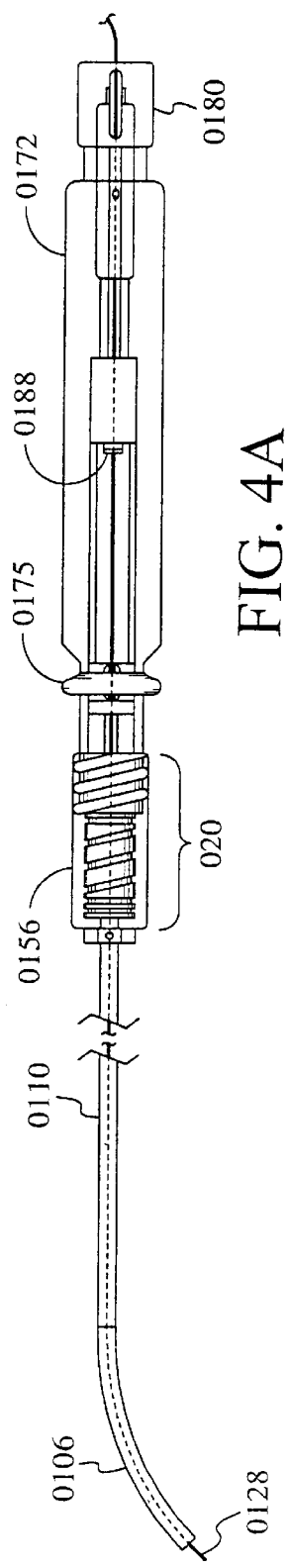
FIGS. 4A–4C are representative isometric cutaway views of the deflectable steerable catheter of the present invention illustrating an embodiment of the method of the present invention.
Figure 4B:
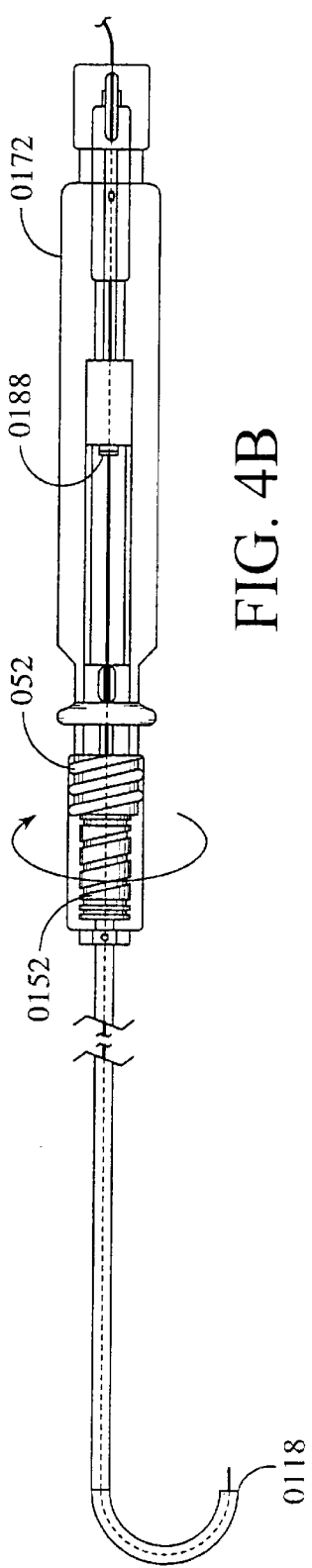
Figure 4C:
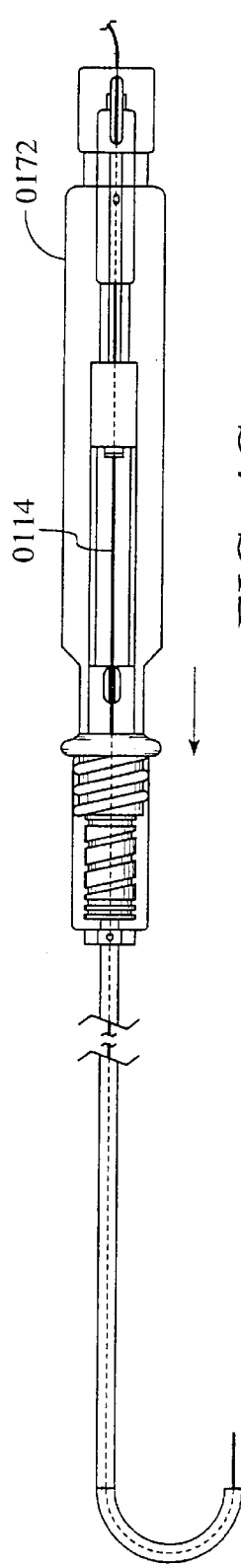

FIGS. 4A–4C show an automatic tip alignment mechanism for a deflectable steerable catheter system using a differential screw mechanism 020 within deflection knob 0156. The differential screw member within the knob 0156 has two differing thread pitches where threads 0152 effectuate tip deflection and threads 052 effectuate tip alignment compensation. When the deflection knob 0156 is turned, a corresponding advancement or retraction of the catheter's outer jacket occurs causing handle section 0172 to move in relation to the proximal region of center or inner tube 0114 and the optical fiber thereby maintaining optical fiber alignment. FIGS. 4A and 4B show the sequential deflection of the distal tip section as the deflection knob 0156 is turned. FIG. 4A shows the catheter distal section 0106 without fiber advance, FIG. 4B shows the distal section 0106 deflected and FIG. 4C shows the distal section 0106 deflected with advancement of optical fiber tip 0128. The diaphragm valve 0188 acts as a seal component to prevent saline solution, if used, from being emitted from the handle while still allowing translation of the optical fiber. An optical fiber is inserted into the inner tube 0114 and the fiber distal tip 0128 and catheter tip 0118 are adjusted and aligned manually prior to use. As the deflectable tip section 0106 is deflected as shown in FIG. 4B, the differential screw in deflection knob 0156 causes relative motion of the catheter jacket 0110 and handle 0172 that is attached to the optical fiber advance mechanism thereby maintaining the alignment between the fiber distal tip 0128 and catheter tip 0118 with the improved auto-alignment knob incorporated in the handle 0172. FIG. 4C shows distal section deflected with the fiber advanced using a ring-type knob 0175 which surrounds the handle section 0172 and facilitates fiber advancement to a preset depth according to a setting made with depth control knob 0180.

FIG. 4D shows a cross-sectional view of the deflection knob 0156 with the catheter base 0162. The threads 0152 for effectuating deflection of the catheter's distal end 0118 are engaged by a pin 025 attached to the deflection knob 0156. The tip alignment compensation threads 052 inside proximal section of the deflection knob 0156 are engaged by another pin 027 attached to the deflection housing tube 0150. The pull wire 0122 is attached at a stop connected to the deflection housing tube 0150. When the deflection knob 0156 is turned, the deflection housing tube 0150 translates over the catheter base 0162. The threads create linear translation compensation of the optical fiber distal tip 0128 as the catheter tip 0118 is deflected.

FIG. 4E is a cross-sectional view of a variation of the embodiment shown in FIGS. 4A–4D using an integrated rotatable differential screw mechanism in deflection knob 0156 that further includes an integrated fiber advance component thereby allowing a physician to maintain hand placement while adjusting the amount of deflection by knob 0156 or while advancing an optical fiber. The design shown in FIG. 4E in cross-section further includes a fiber advance annular knob 0256 that slides over and rotates with the deflection knob 0156. This sliding aspect is achieved by longitudinal slots 0252 in the outer surface of the deflection knob 0156 and corresponding longitudinal slots in the annular knob 0256. The fiber advance annular knob 0256 replaces the fiber advance knob 0175 shown in FIGS. 4A–4C above. Rotation of the optical fiber advance knob 0256 rotates the deflection knob 0156. Linear advancement of the fiber advance knob 0256 alone without rotation of the deflection knob 0156 advances the optical fiber without tip deflection due to the longitudinal slots 0252 in the deflection knob 0156 guiding longitudinal slots in the fiber advance knob 0256. The advancement of the fiber is achieved through a fiber advance collar 0275 that is attached to the advance slider. The fiber advance knob 0256 has a return spring 0276.

Figure 4F:
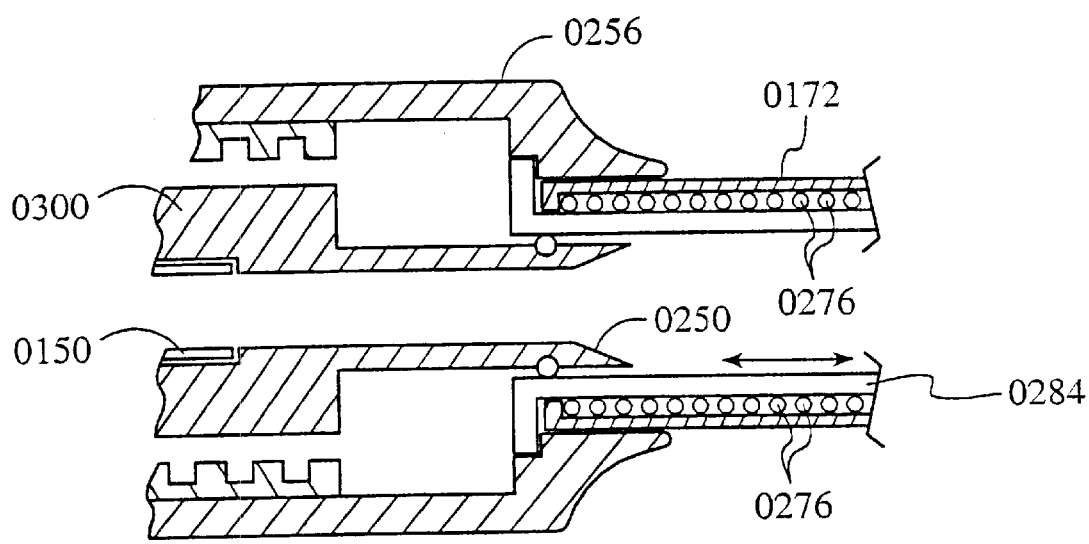
FIG. 4F is a cross-sectional view of a variation of an O-ring sealing member for the optical fiber for the present invention.

FIG. 4F is a cross-sectional view of an alternate design for the functional requirements of the diaphragm valve 0188 sealing device for use with the catheter handle concepts shown in FIGS. 4A–4E. The sealing device is an O-ring 0250 that is disposed about a central member 0300 where the optical fiber translates within the central member 0300. This central member 0300 is attached to the deflection housing tube 0150. An annular extension member 0284 is attached to the advance slider 0184 shown in FIG. 4B and slides along on the external side of O-ring 0250 to maintain the fluid seal. An equivalent sealing member of O-ring 0250 is a quad seal. The O-ring seal operates comparable to a "syringe" type device.

The following description of the mechanical operation of the deflectable steerable catheter 100 of the present invention is intended for illustrative purposes only, and is not to be construed in any way as limiting the scope of subject matter claimed herein. Reference is made to all of the figures.

As described above, the deflectable steerable catheter of the present invention has a tip deflection mechanism as well as a functional device tip alignment mechanism. With regard to FIGS. 1, 2 and 3, rotation of the actuator 156 in a clockwise direction, i.e., as viewed from a proximal end, will effect corresponding rotation of inner deflection knob 154. Since the actuator 156 and inner deflection knob 154 are rotated relative to the handle 170, and the catheter base 162 is keyed to the deflection actuator 150 by ribs 192 engaging grooves 194 along with the deflection actuator 150 being keyed to the handle 170 by ribs 196 sliding into grooves 198 thereby preventing rotational motion as between the handle 170, the deflection actuator 150 and the catheter base 162, said clockwise rotation will cause proximal translation of deflection actuator 150 by pins 140 riding in helical groove 152, as deflection actuator 150 is moved linearly in a proximal direction, tension in the pull wire 122 acts on the distal tip 118 of the deflectable steerable catheter 100 and causes deflection thereof.

Operation of the automatic functional device tip alignment mechanism is based on a screw thread pitch differential. Without the tip alignment feature of the present invention as deflection of the deflectable portion 106 of the catheter 100 occurs the orientation of the distal tip 118 of the catheter 100 and the distal tip 102 of the functional device would be modified such that any pre-existing alignment would be lost. The cause of this loss of alignment between the distal tip 118 of the catheter 100 and the distal tip 102 of the functional device upon deflection of the deflectable portion 106 is caused by retraction of the pull wire 122, causing an apparent change in the length of the elongated catheter jacket 110 and a displacement of any pre-existing alignment between the distal tip 118 of the catheter 100 and the distal tip 102 of the functional device.

Therefore, to compensate for these alignment disrupting forces, screw threads having a differential in pitch size are used. With reference to the drawings, as mentioned above, deflection of the deflectable portion 106 of the catheter 100 is caused by clockwise rotation of the actuator 156 and inner deflection knob 154. Said clockwise rotational motion of actuator 156 and inner deflection knob 154 causes distal linear translation of inner deflection knob 154, proximal hub 166 and catheter base 162 thereby causing compression of the outer catheter jacket 110 and proximal linear translation of deflection actuator 150 and pull wire stop 168 thereby increasing tension in pull wire 122 and causing deflection of the deflecting portion 106. Simultaneously, as will be apparent by an inspection of the drawings, as inner deflection knob 154 is rotated clockwise by actuator 156, external helical thread 174 on the handle 170 engaged by internal helical groove 176 within inner deflection knob 154 causes simultaneous translation of the handle 170, thus slightly moving the fiber 116, or other functional device, and thereby compensating for the effective change in length of the outer catheter jacket 110 by maintaining alignment between the distal tip 118 of the catheter 100 and the distal tip 128 of the laser energy delivery device 116, or other functional device.

In the case of laser assisted PTMR or other procedures, intervention occurs when an optical fiber, fiber bundle or other laser energy delivery device 116, or other functional device, is advanced through the inner tube 114 of the deflectable steerable catheter and into the patient. Fiber advance is effected in one of two ways—by manually urging in a distal direction either back flange 220 of depth stop 210 or actuator 156. In either case, the fiber, fiber bundle or other laser energy delivery device 116 or other functional device being held firmly in place at the proximal end by Touhy-Borst type fitting 216 advances distally along with the back tube 182 and the front tube 180, both sliding over the inner tube 114, the bushing pins 186 extending from the pin seats 190 in the front tube 180 contained by and riding within the slots 188 located distally on the handle 170, thus placing the spring 200 into increased compression. Retraction of the fiber 116 decreases the compressive forces on the spring 200.

The deflectable steerable catheter of the present invention, access port cover plate 222, as shown in FIGS. 1, 1A and 2 can be removed and any operative device, electrical contacts such as thin coaxial or other electrical traces, leads, conductors, etc. can lead through at least the outer catheter sheath and be utilized at any of various positions on the handle 170, elongated portion 110 or distal tip 118 of the deflectable steerable catheter 100 of the present invention. In particular, the distal tip 118 can be provided with a positioning sensor or visualization device, for providing any of various signals from any of various types of sensor or analyzer equipment, such as the ultrasound ranging methods and devices shown and described in U.S. patent application Ser. No. 08/852,977 filed May 7, 1997 and continuation-in-part application Ser. No. 09/169,747 filed Oct. 9, 1998 entitled ULTRASOUND DEVICE FOR AXIAL RANGING, both of which are hereby incorporated by reference in their entirety. In a preferred embodiment, an annular ultrasound transducer is positioned distally on the distal tip of the catheter 118 to transmit ultrasound signals substantially perpendicular to tissue, the transducer further receiving returning signals from the tissue to be treated.

Figure 5:
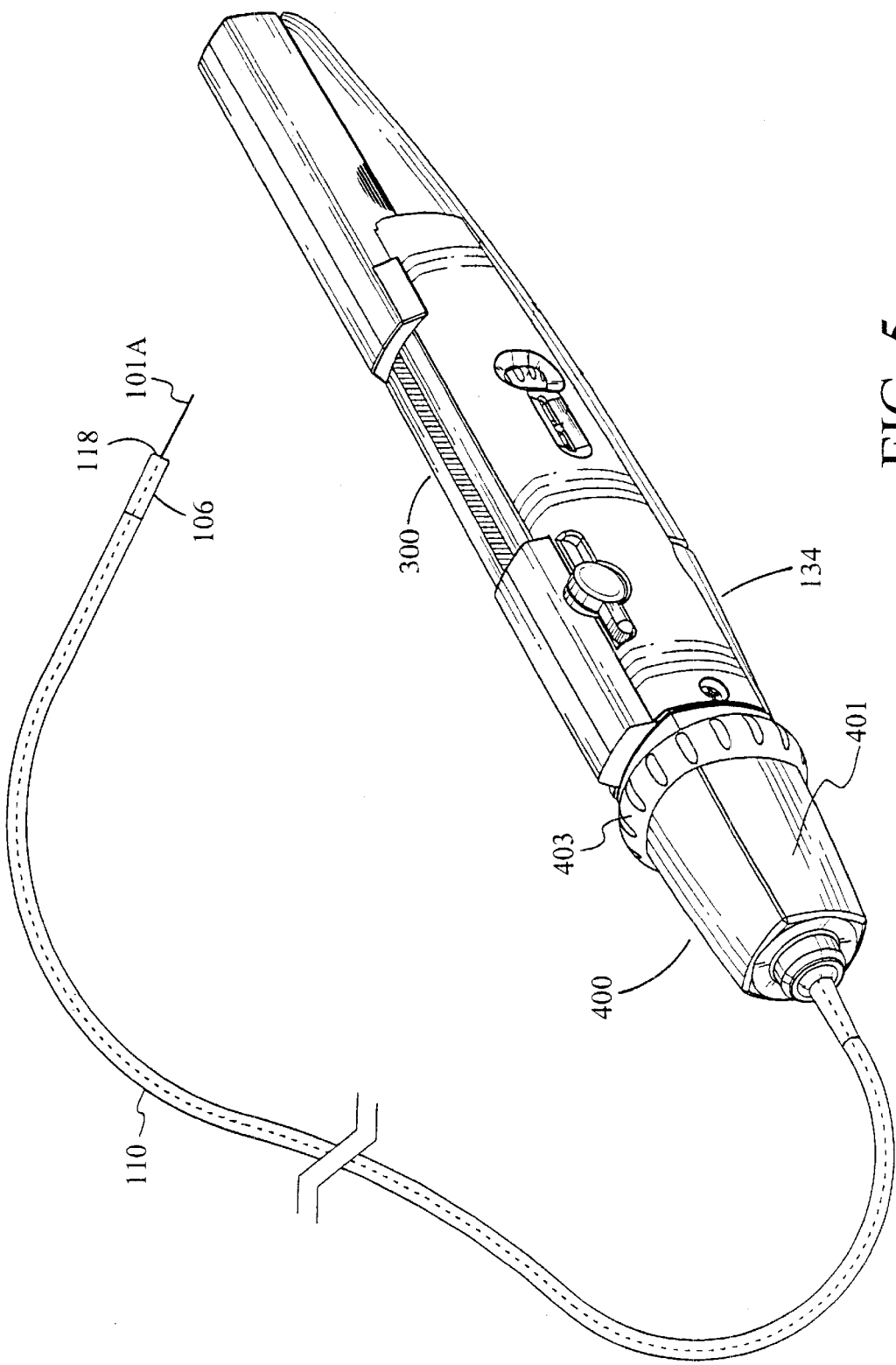
FIG. 5 is a representative view of an alternate embodiment of the proximal portion of the non-deforming deflectable catheter of the present invention incorporating an automated drug delivery module.

FIG. 5 is a representative view of an alternate embodiment of the proximal portion 149 of the non-deforming deflectable catheter 100 of the present invention incorporating an automated drug delivery module 300. U.S. patent application Ser. No. 09/080,175 (MH1), incorporated by reference in its entirety, teaches a drug delivery module with a piercing needle for percutaneous catheter based procedures. The drug delivery module 300 enables a user to both extend a piercing needle 101A, having a bevel cut end tip or other operable tip for piercing tissue, and dispense drug or other agent there through, with a single, manual draw or squeeze force applied to a trigger 134. The drug delivery module 300 is attached to the proximal end of the deflection and autoalignment assembly 400. A delivery tube or conduit 101 (not shown) extends from module 300 through the elongated catheter jacket 110 to the distal tip 118 of the nondeformable deflectable catheter. Flow of liquid, solid or vapor phase drug, solution or other agent or compound is communicated from the module 300 through the delivery tube and is dispensed through piercing drug delivery needle 101A subsequent to advance of drug delivery needle 101A through the distal tip 118 of catheter 100. The delivery tube or conduit 101 with piercing needle 101A is inserted through the working channel or lumen 119 of the inner tube 114 of the catheter to treat the desired number of drug delivery tissue sites. The drug flow is communicated from a reservoir through delivery tube 101 and is dispensed through piercing needle 101A. The non-deforming deflectable portion 106 and distal tip 118 of the catheter can be oriented by deflection and auto-alignment assembly 400.

Figure 6:
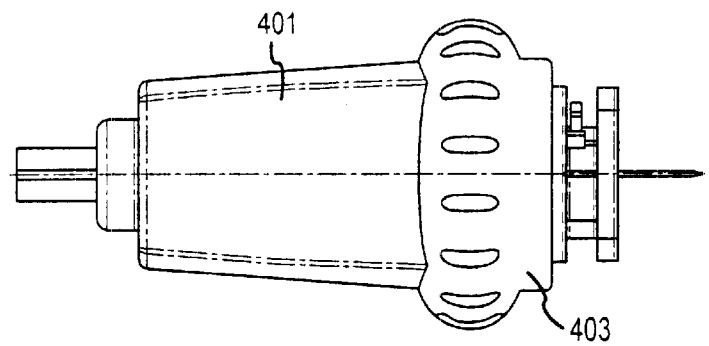
FIG. 6 is a representative side view of a deflection and auto-alignment assembly for use with the drug delivery module as shown in FIG. 5.
Figure 6A:
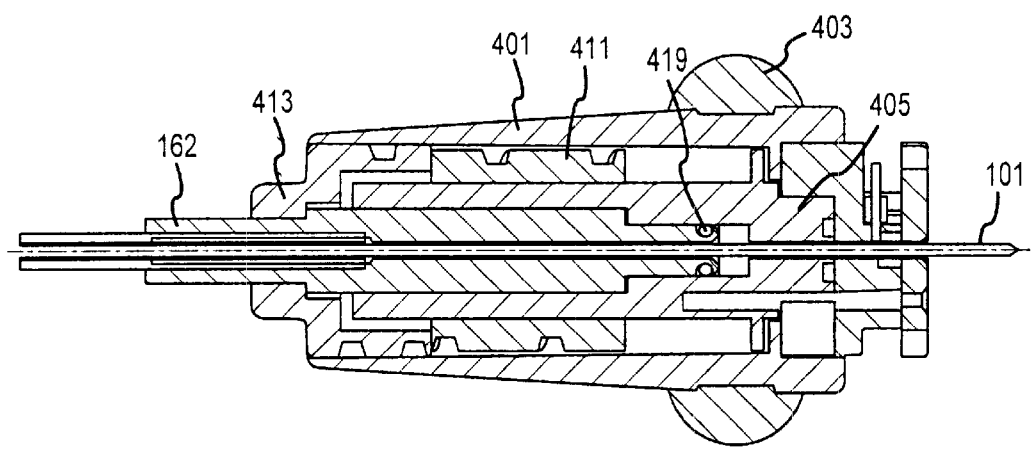
FIG. 6A is a representative section view of the assembly shown in FIG. 6.

FIG. 6 is a representative side view of a deflection and auto-alignment assembly 400 using a rotatable relative movement compensation mechanism for achieving autoalignment of the distal end of the catheter 118 and functional device, specifically the advanced distal tip of drug delivery tube 101A when the catheter is in a deflected position. FIG. 6A is a representative section view of the assembly shown in FIG. 6.

Figure 6B:
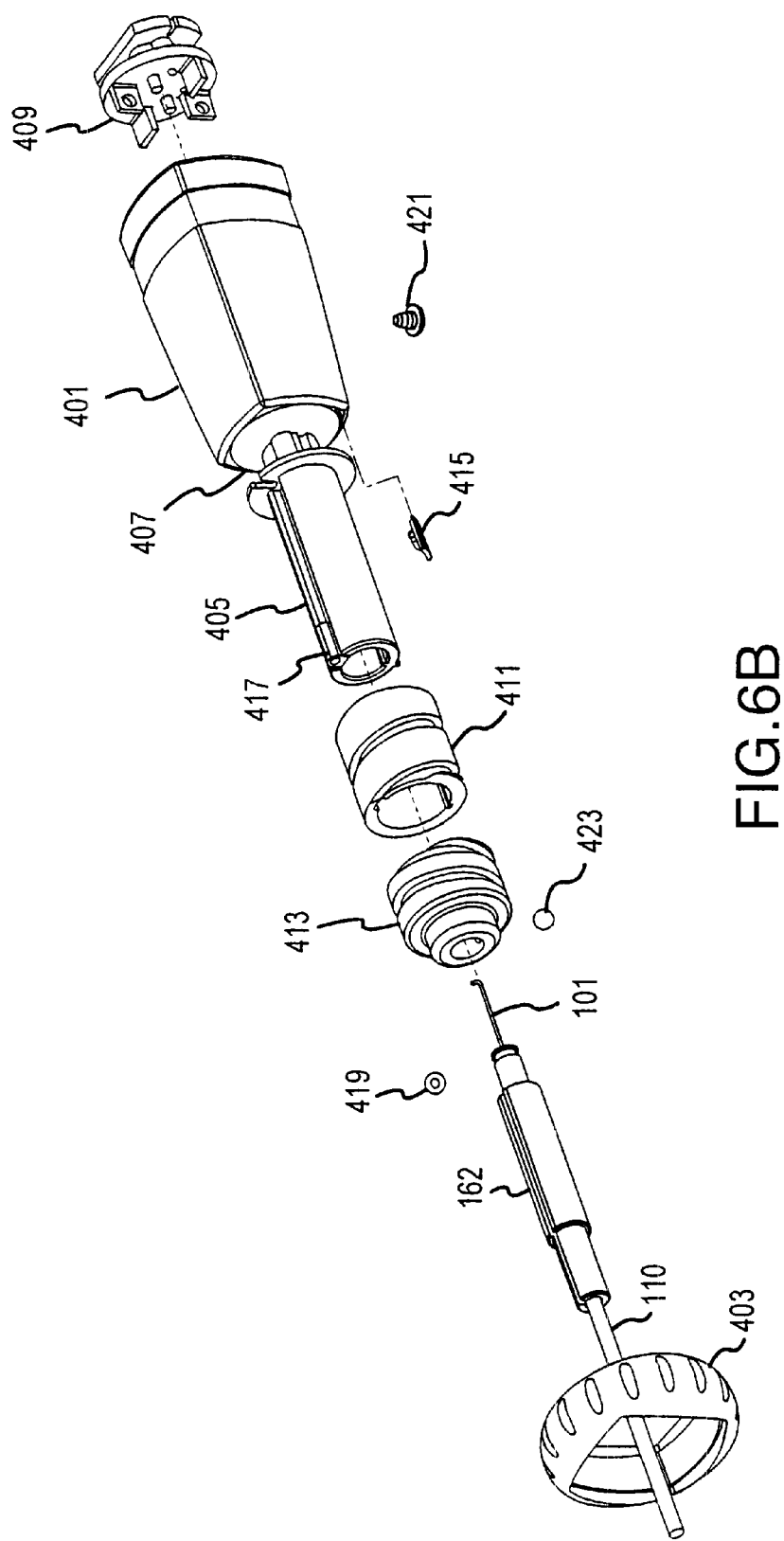
FIG. 6B is a representative exploded isometric view of the assembly shown in FIG. 6.

FIG. 6B is a representative exploded isometric view of the assembly shown in FIG. 6. Steering knob 401 is captured by lead screw guide 405, wave washer 407 and interface 409. Lead screw 411 moves axially on lead screw guide 405 constrained by a ridge on the lead screw guide 405 and a corresponding slot in the lead screw 411. Back thread screw 421 couples the lead screw 411 to the steering knob 401. Lead screw 411 has external threads that couple with the back thread screw 421. Threaded cap 413 is the attaching member for the exterior portion of the catheter base 162. The elongated catheter or outer jacket 110 is mounted into catheter base 162. Front thread screw 415 is fixed to steering knob 401. Threaded cap 413 is mounted into steering knob 401 with front thread 415 riding in threads of the threaded cap 413. Catheter base 162 is inserted within lead screw guide 405. Set screw 423 fixes catheter base 162 to threaded cap 413. In a completed assembly, the lead screw 411 can be moved in a linear fashion to articulate the distal tip of the catheter device by rotation of steering knob grip 403 situated on the exterior of the steering knob 401. Inner tube 114 (not shown) is located inside catheter base 162 and ends at the proximal end of the catheter base 162.

Articulation of the catheter tip 118 is accomplished by push-pull forces on the pull wire 122 (not shown) extending between the distal tip 118 and the lead screw 411, co-extensively extensively and/or coaxial with catheter jacket 110. The pull wire 122 is coupled into pull wire holder 417 that secures the pull wire 122. The pull wire holder 417 is constrained to axial movement by riding in a slot in the leadscrew guide 405. The pull wire holder 417 moves axially by the travel of the adjacent leadscrew 411. Simultaneous with movement of the leadscrew 411, the threaded cap 413 moves in the opposite direction effectively providing a forward relative movement of the catheter jacket 110 as the catheter tip 118 is deflected.

Figure 7:
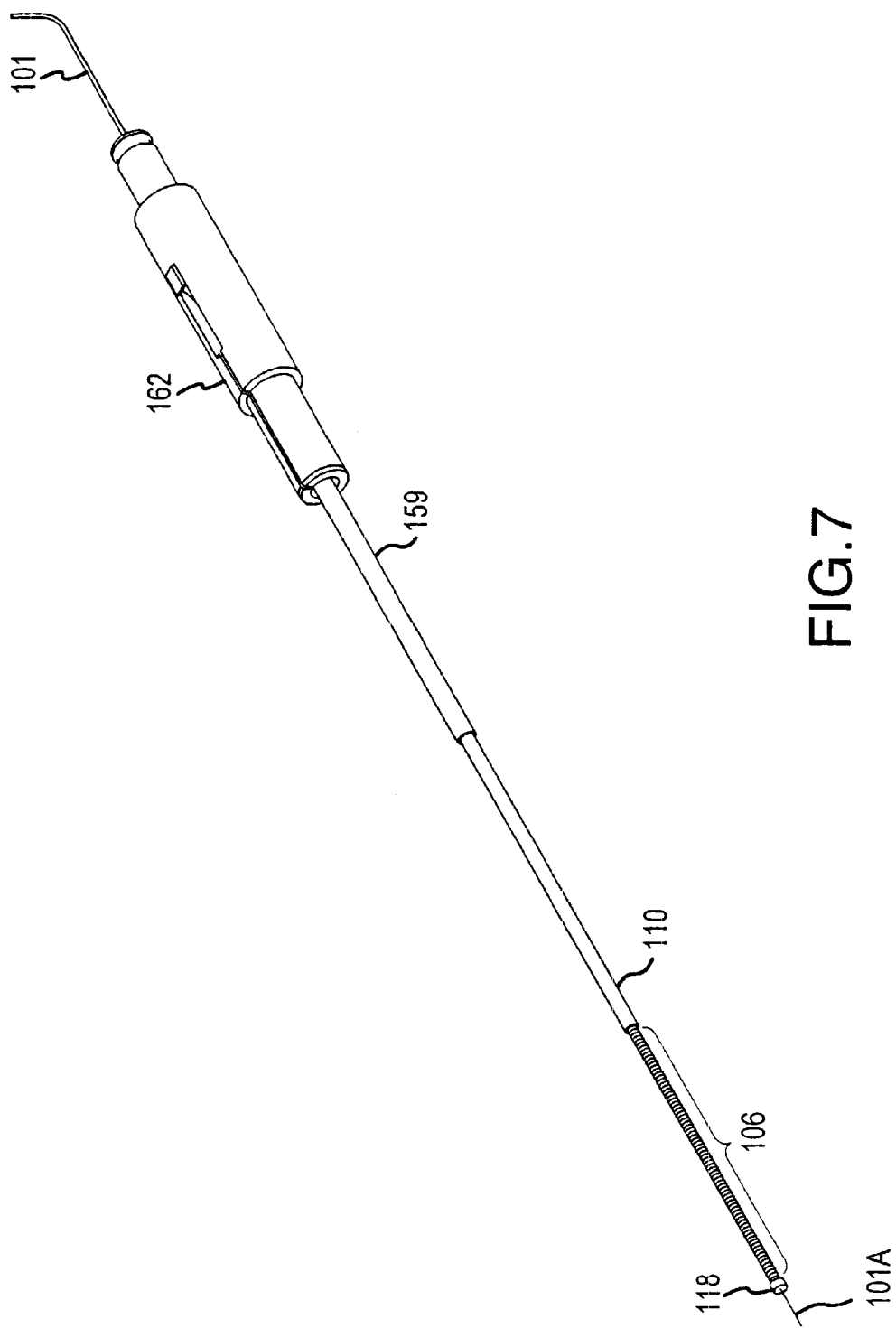
FIG. 7 is a representative isometric view of the preferred embodiment of the nondeforming deflectable multi lumen catheter of the present invention with delivery tube.
Figure 7A:
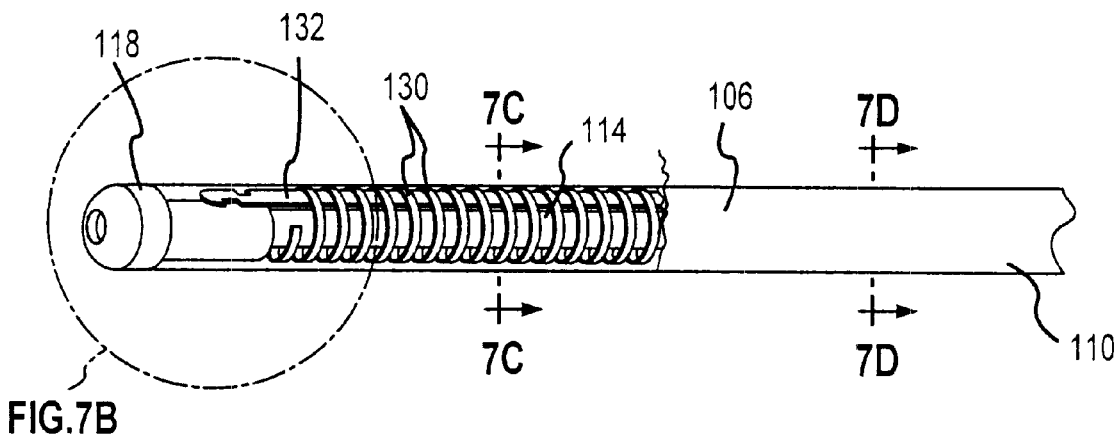
FIG. 7A is a representative partial cutaway view of the deflectable distal portion and tip of the embodiment of the catheter shown in FIG. 7.

FIG. 7 is a representative isometric view of the preferred embodiment of the non-deforming deflectable multi-lumen catheter 100 of the present invention. Shown are the distal tip of the catheter 118, deflectable distal portion of the catheter 106, elongated catheter 110, proximal strain relief 159 and delivery tube 101 with egressing distal piercing needle tip 101A. FIG. 7A is a representative partial cutaway view of the deflectable distal portion 106 and tip 118 of catheter 100. FIG.7AA is a representative isometric view of the embedded coil extending the length of the deflectable distal portion of the catheter 106, from the proximal end 131 of the distal tip 118 to the proximal end 133 of the deflectable portion of the catheter 106. FIG. 7AAA is a representative isometric view of shim 132, as shown in FIG. 7A, with holes at the distal and proximal ends to promote embedding into the polymer wall.

Figure 7B:
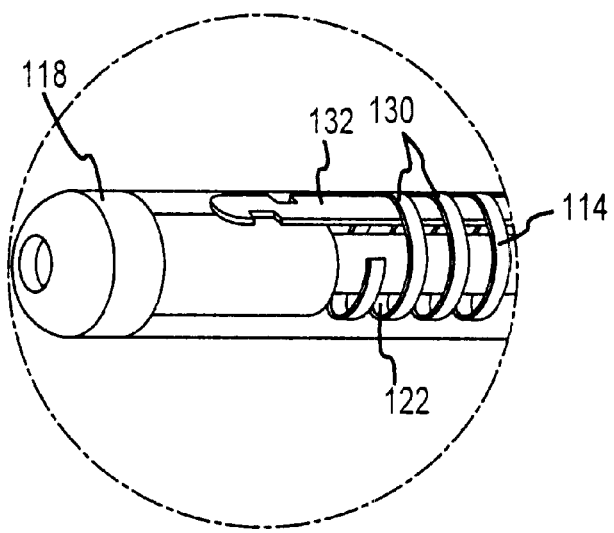
FIG. 7B is an enlarged representative partial cutaway view of the deflectable distal end portion and tip of the embodiment of the catheter shown in FIG. 7.
Figure 7C:
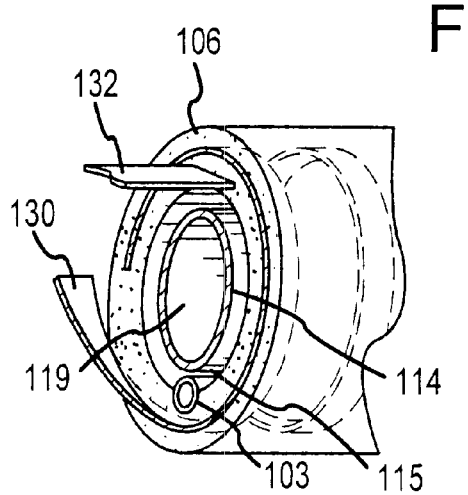
FIG. 7C is an enlarged representative isometric section view of the deflectable distal portion of the embodiment of the catheter shown in FIGS. 7 and 7A.

FIG. 7B is an enlarged representative partial cutaway view of the deflectable distal end portion and tip of the embodiment of the catheter 100 shown in FIGS. 7 and 7A with embedded flat shim 132 and coil 130 and catheter tip 118. In FIG. 7C, inner tube 114 is made of plastic with a high degree of lubricity, to allow the functional device to slide with minimal friction, and extends the length of the distal portion of the catheter 110, including deflectable portion 106, and into the proximal portion. Inner tube 114 supports the functional device, such as drug delivery tube 101, against buckling under column loading. Saline may be delivered through the inner tube lumen 119 and from the distal tip of the catheter 118. FIG. 7BB is a representative isometric detail view of the assembly of the deflectable distal end portion 106 of the embodiment of the catheter shown in FIG. 7B further showing pull wire 122 with distal attachment point 137 and drug delivery tube 101, with piercing needle distal tip 10A and coupling member 139, coupling the needle 101A and drug delivery tube 101. Pull wire 122 is securely coupled, typically soldered or welded at attachment point 137 and extends through pull wire lumen 103 for attachment to the proximal portion of the catheter. As pull wire 122 is pulled, a force is applied to the catheter tip 118 resulting in tip deflection perpendicular to the plane of the shim 132.

FIG. 7C is an enlarged representative isometric section view of the deflectable distal portion 106 of the embodiment of the catheter shown in FIGS. 7 and 7A showing the shim 132 and coil 130 embedded in the catheter or outer jacket 106, eccentric pull wire lumen 103, outer catheter lumen 115 and substantially co-axial inner tube 114 with lumen 119. Inner tube 114 extends the length of deflectable distal end portion 106 from the distal tip 118 to the proximal portion of the catheter 149 and forms lumen 119 through which a functional device is advanced. FIG. 7CC is another representative isometric detail view of the assembly of the distal end of the catheter 100 shown in FIG. 7C further showing pull wire 122.

Figure 7D:
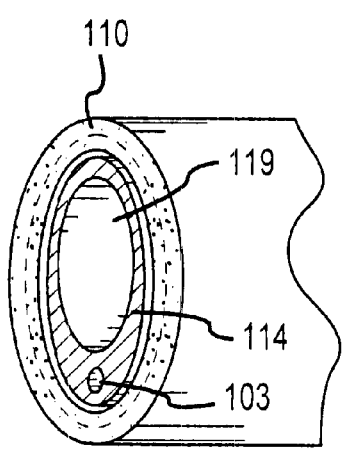
FIG. 7D is an enlarged representative isometric section view of the proximal portion of the embodiment of the catheter shown in FIG. 7.
Figure 7B:
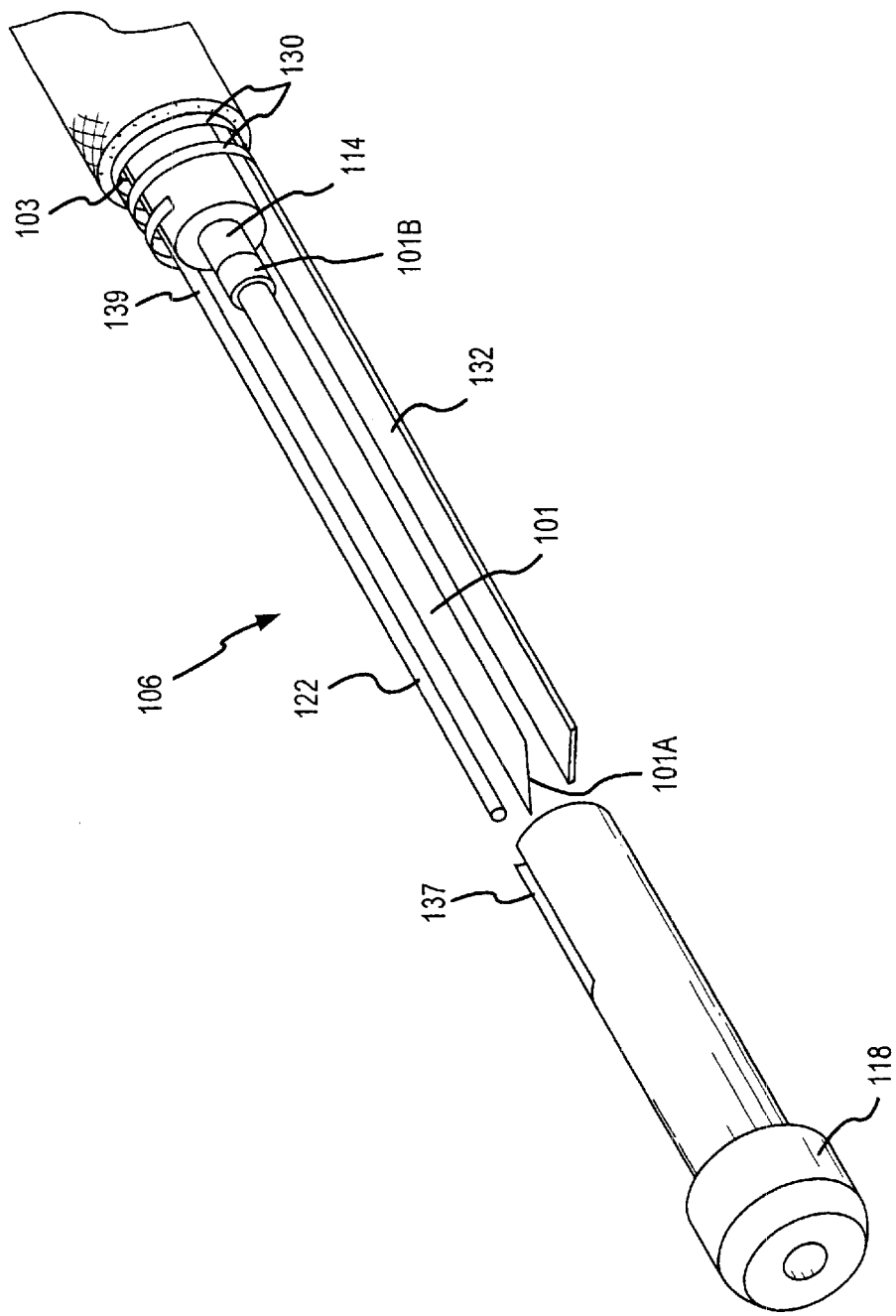
Figure 7C:
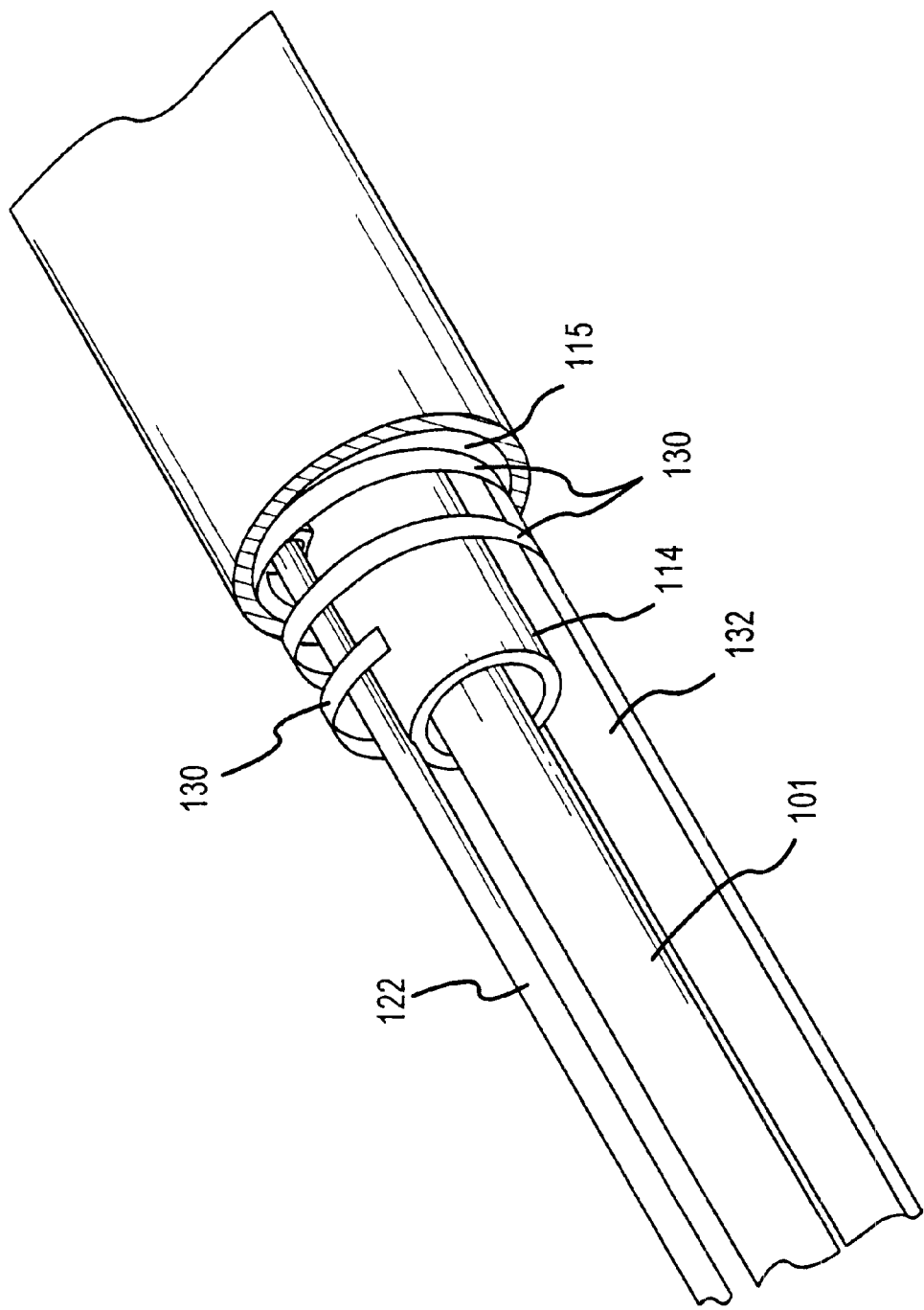

FIG. 7D is a representative isometric section view of a proximal portion of braided catheter jacket 110 as shown in FIGS. 7 and 7A. Inner tube 114 forms lumen 119, within which the functional device (not shown) is disposed and an embedded pull wire lumen 103 within which pull wire 122 (not shown) is contained. The multi-lumen inner tube extends proximally from the junction of the deflectable end portion 106 (not shown) along the entire length of the proximal catheter jacket 110. Pull wire lumen 103 isolates the pull wire 122 from the functional device housed in lumen 119 and prevents contamination. Pull wire lumen 103 further acts to guide pull wire 122 and prevent buckling, "S-ing", or deformation of the distal portion 106 as the catheter is deflected.

Figure 7E:
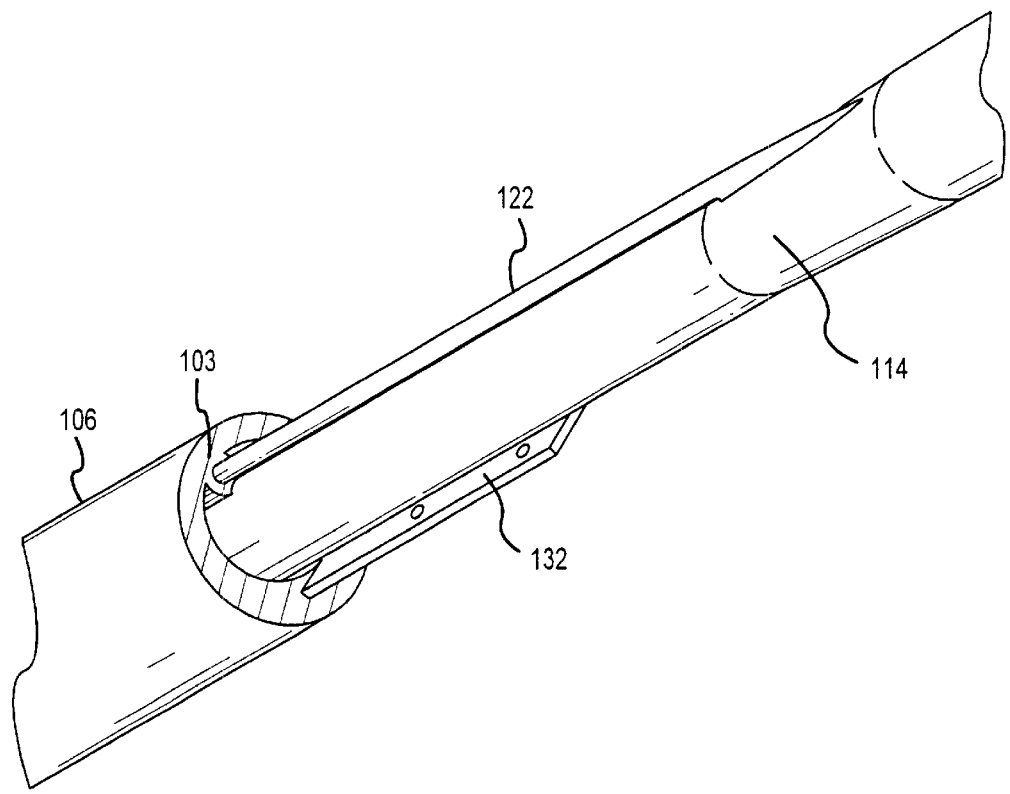
FIG. 7E is a representative isometric detail view of the assembly of the pull wire lumen at the junction of the distal and proximal portions of the catheter jacket of the embodiment of the catheter shown in FIG. 7AA.
Figure 7F:
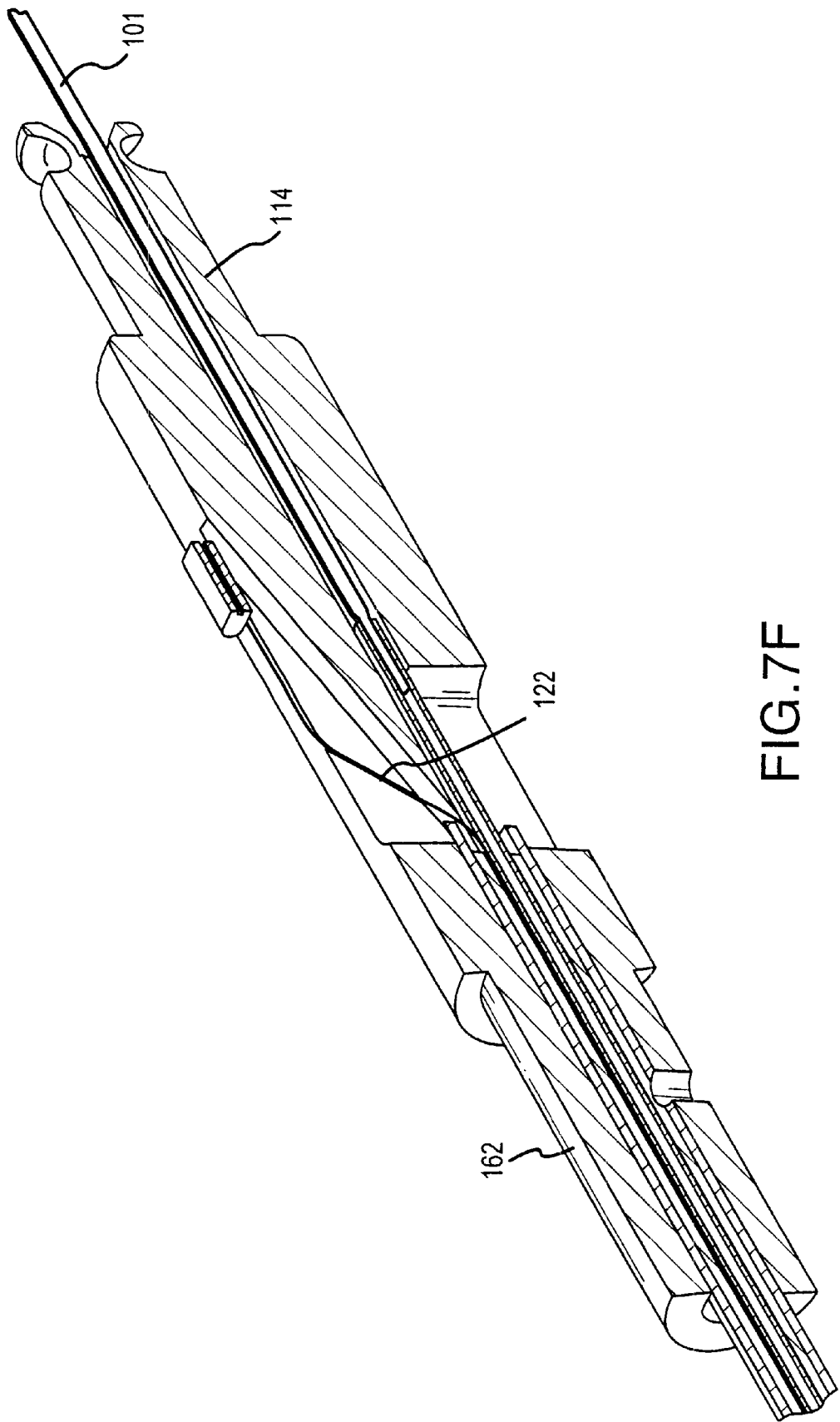
FIG. 7F is a representative isometric detail view of the assembly of the proximal portion of the catheter as shown in FIG. 7.

FIG.7E is a representative isometric detail view of the assembly of pull wire lumen 103 at junction 133 (shown in FIG. 7AA) of distal and proximal portions of the elongated catheter jacket 110. Pull wire lumen 103 is an eccentric or off-center lumen running the length of deflectable distal portion 106, and is at least partially embedded, although it may be fully embedded, in the wall of the outer jacket portion 106. FIG. 7E shows the transition of eccentric pull wire lumen 103 from at least partially embedded in the wall of the outer jacket at the deflectable distal portion 106 to fully embedded in the wall of the inner tube 114 at the proximal portion of the elongated catheter. FIG. 7F is a representative isometric detail view of the assembly of the proximal portion of the catheter as shown in FIG. 7. Shown are the proximal portions of shim 132, pull wire 122, delivery tube 101 and catheter base 162.

Referring to FIGS. 7–7F, catheter 100 is a multi-lumen catheter. The outer jacket lumen 115 extends the entire length of the outer jacket 110, including deflectable distal portion 106. Inner tube lumen 119, is the main working lumen and in which the functional device, such as a laser energy delivery device 116, or delivery tube 101 is disposed. A second, typically smaller, eccentric pull wire lumen 103 segregates pull wire 122 from lumen 119 and any functional device and/ or saline inserted therein. Pull wire lumen 103 is at least partially, and alternatively may be fully embedded in the wall of the catheter or outer jacket 110 at the deflectable distal end 106. In the preferred embodiment, pull wire lumen 103 transitions proximal to the deflectable distal end, becoming an eccentric fully embedded lumen in the wall of inner tube 114. In an alternate embodiment, pull wire lumen 103 remains partially or fully embedded in the wall of outer jacket 110 for the entire length of the distal portion of the catheter.

Further in the preferred embodiment, coil 130, shim 132 and pull wire lumen 103 are at least partially embedded, encased, or extruded in a, thereby creating a flexible composite catheter structure having a steerable tip and minimized profile, or diameter. The steerable distal end of the catheter is flexible for maneuvering through the vasculature and kink resistant when bent up to about 270 degrees. This allows for the functional device, such as a drug delivery tube 101, to be advanced in and out of the catheter without friction, and to lower the pull forces needed on pull wire 122 to bend the tip of the catheter. When tension is applied to confined pull wire 122, the distal portion of catheter bends in a essentially circular or coil fashion rather than into an undesirable deformed s-shape. It will be understood that the term non-deforming is intended to refer to the undesirable "S" shape and other deformations which occur in deflectable catheters of the prior art, such as described above. The pull wire lumen 103 is located radially closer to the central axis of the catheter than the coil allowing for greater forces to be applied to the pull wire without failure of the extrusion wall. Coil 130 is preferably, but not essentially, flat and made of metal such as steel, platinum or nitinol, and acts to reinforce the extruded wall of distal portion 106 and contain the pull wire, thereby preventing it from breaking through the wall under high load. Shim 132 is located opposite pull wire lumen 103 and allows distal portions 118 and 106 to deflect without veering to the left or right of elongated catheter 110. Embedding either or both the coil and the shim will create a polymer/metal composite. The metal/polymer composite created by embedding the shim allows for a higher resistance to torsion than a non-embedded shim. This resistance to torsion is variable and controllable through the selection of the properties of materials of both the plastic and shim material properties. In alternate embodiments of the invention, the embeddedness of either or both the shim and the coil, may be varied as long as they are at least partially embedded.

The deflectable distal portion 106 and outer jacket 110, and inner tubel 14 are constructed of one or more biocompatible polymers. This includes both thermoplastic or thermosetting plastics, for example, but not limited to, polyamides, such as nylon, polyethylenes and polyurethanes of varying stiffness or flexibility. The polymers may be of varying lengths, varying densities, such as low or high density polyethylene, and/or reinforced with other materials for increased resiliency. The plastic may be formed by any process known to those with skill in the art, for example extrusion.

The polymer of the proximal portion of the elongated outer catheter 110 is stiffer than the steerable, flexible deflectable distal end 106. The elongated outer catheter 110 is a stiff braided tubing enabling push, torque, kink resistance and high burst pressure. The proximal end of the deflectable distal portion, as shown in FIG. 7C, may be comprised of a stiffer plastic than that of the distal end, as shown in FIG. 7B. Preferably both would still have a greater flexibility than that of the elongated catheter 110 to create appropriate transitions for a non-deforming shape. Using a polymer such as a low stiffness polyurethane may be advantageous to create, for example, a softer distal tip with a high stiffness polymer for the proximal portion of the inner tube.

The catheter may be of any size but is preferably in the range of 4 to 9 French.

At least partially embedding shim 132 and pull wire lumen 103 at the deflectable distal end of the catheter provides the necessary mechanical stability and alignment in lieu of an anchor sleeve as shown in U.S. patent application Ser. No. 09/156,963 and 964 (P71 and MH2).

As will be understood by the drawings and description herein, the curvature in the deflectable end portion 106 and inner tube 114 can be varied. Pull wire 122 is attached at a location 137 near the tip 118 and extends through pull wire lumen 103. The deflectable end portion 106 is made out of a softer material or materials than the proximal catheter jacket 110. As the pull wire 122 is pulled, a force is applied to the catheter tip 118 resulting in tip deflection. This design relies upon the flexibility of the polymers used, the flexibility of the coil 130 and also the return force of the shim 132. Increasing the tension in (or retracting) pull wire 122, attached at 137 at the catheter tip 118, applies a force to the catheter tip 118 and the deflectable end portion 106 in a direction essentially out of and toward a position perpendicular to the undeflected flat plane of the shim 132. Continued retraction of the pull wire 122 will cause continued deflection of the catheter tip 118 and end portion 106, with useful ranges of deflection between about 0 and about 180 degrees (U shape) to about 270 degrees (pig-tail shape), or more or less depending upon construction. The helical coil 130 can be constructed with varying degrees of flexibility and pitch, and with any number of coils, to effect intended curvature of the deflectable tip. Coil 130 in any of these figures may be made of various materials known to those of skill in the art including, but not limited to, stainless steel, tungsten, or even partially or completely constructed of one or more super elastic and/or shape memory materials. Cross section of coil 130 may be for example, helical, oval, round, rectangular or flat ribbon. As noted previously, the materials selected for the outer jacket, and other portions of the catheter 100, provide a predetermined and controllable stiffness to the system. Various combinations of polymers of different lengths and flexibility yield different curves, more rounded portions, etc. Thus, it will be possible to form less invasive, atraumatic shapes at the distal end. Thus, bending the distal portion 106 of the catheter 100 about 180° to about 270° will allow the practitioner to present a rounded, atraumatic section that will pass easily through the aortic valve. The catheter 100, once inside the ventricle, can also be bent and can access more easily all sides and areas of the ventricular walls due to large bending angles. Inside the ventricle, the distal tip of the catheter 118 is pressed against a ventricular wall and the distal tip of the functional device, such as delivery tube 101 or laser energy delivery device 116, is advanced into the ventricular wall. Additionally, with the automatic tip compensation mechanism, the distal tip of the functional device remains aligned with the distal tip of the outer jacket or catheter 118.

It will be further understood that shim 132 can also be provided with varying degrees of stiffness. As shim 132 is bent, it may form a predetermined shape or bend in certain portions more readily or sooner than others. Therefore, shim 132 provides variable stiffness in a specific plane, i.e., predetermined and/or varying flexibility throughout its length. As best shown in FIG. 7AAA, shim 132 may have one or more holes passing there through to enhance embedded stability within the distal end 106.

It will be understood by those skilled in the art that any or various of the components of the present invention can be formed using a radio opaque material of construction. Visualization of portions of the catheter, including but not limited to coil 130, shim 132, distal tip 118, deflectable portion 106, and inner tube 114 may be desirable or otherwise useful with, for example, fluoroscopy. Additionally, portions of the plastic catheter jacket and/or inner tube may be loaded with varying types or degrees of opacifying material to provide enhanced and unique visualization and recognition. A teaching of radio opaque markers with catheters can be found in U.S. patent application Ser. No. 09/107,843 entitled INTRA-CORPOREAL DEVICE WITH RADIO OPAQUE MARKER filed Jun. 30, 1998 (P0063.0) and U.S. Provisional Application Serial No. 60/088,018 entitled ENHANCED VIEWING FOR MYOCARDIAL REVASCULARIZATION USING COMPUTER BASED FLUOROSCOPY VIEWING filed Jun. 4, 1998, both of which are hereby incorporated by reference in their entirety.

Figure 8A:
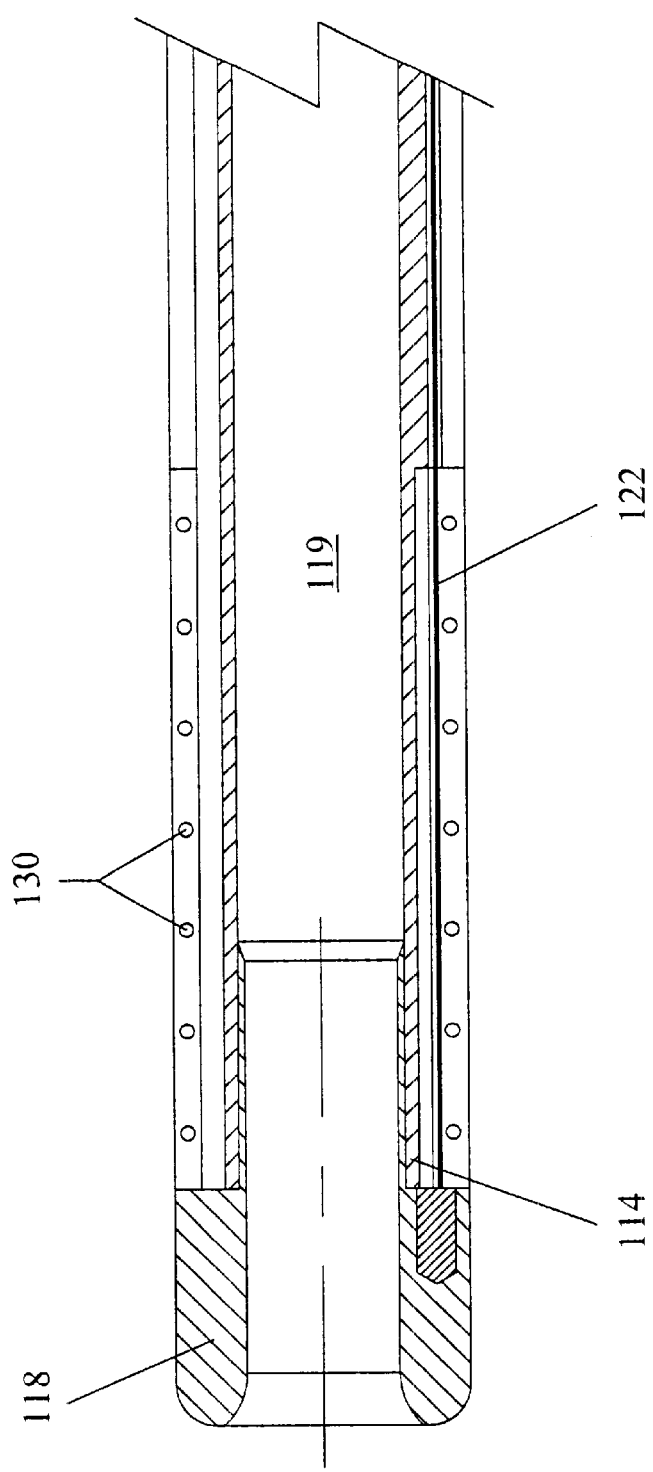
FIG. 8A is a representative section view of an alternate embodiment of the deflectable distal end portion of the non-deforming deflectable catheter of the present invention with an embedded coil and without a shim.
Figure 8B:
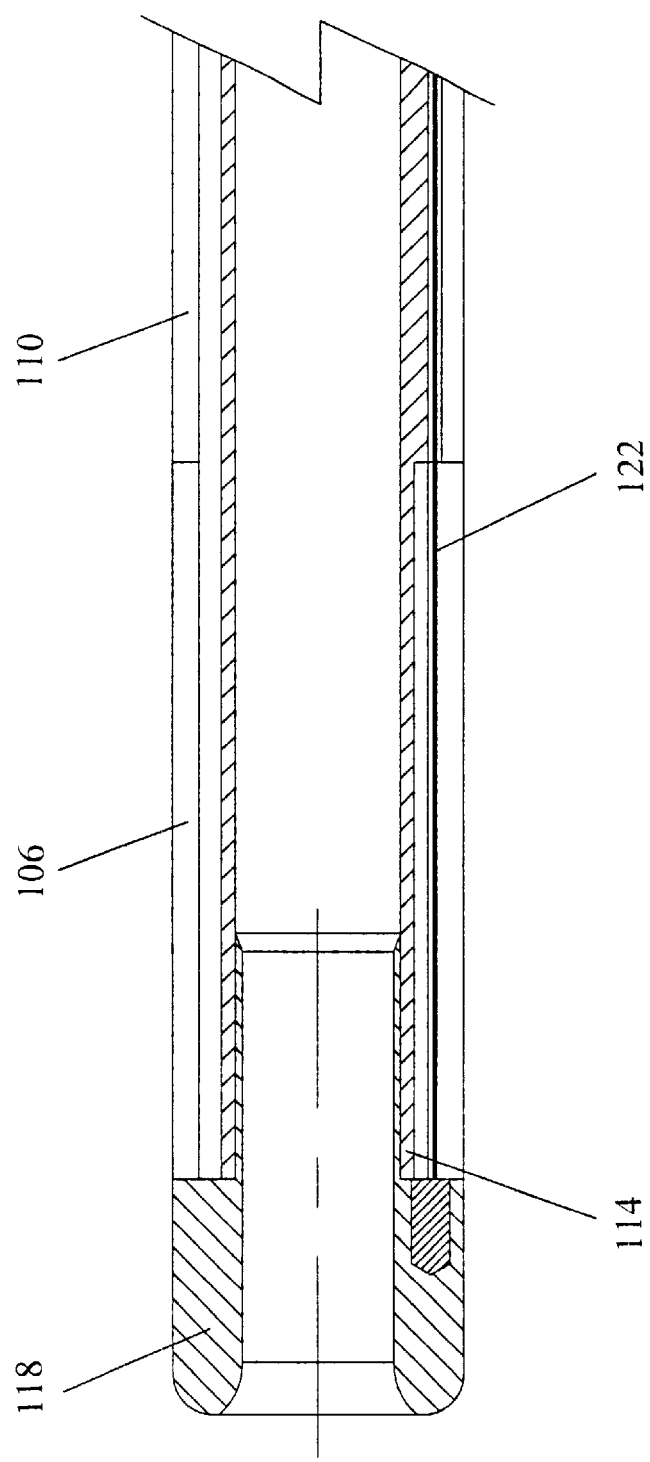
FIG. 8B is a representative section view of an alternate embodiment of the deflectable distal end portion of the non-deforming deflectable multi lumen catheter of the present invention without an embedded coil and without a shim.

FIGS. 8A–8E teach alternate embodiments of the deflectable distal end portion of the catheter. FIG. 8A is a representative section view of an alternate embodiment of the deflectable distal portion 106 of the non-deforming deflectable catheter of the present invention having an embedded coil, 130, a pull wire, 122, and pull wire lumen, 103, but no shim. FIG. 8B is a representative section view of an alternate embodiment of the deflectable distal end portion 106 of the non-deforming deflectable catheter of the present invention having pull wire 122 and pull wire lumen 103 but without either a shim or a coil. While any functional device as defined herein is useful in combination with the catheter, use of a laser energy delivery device, especially an optical fiber or optical fiber bundle, would be particularly advantageous with alternate embodiments in FIGS. 8A–8B. The laser energy delivery device would provide additional support and structure for the distal portion of the catheter in the absence of the coil and/or shim.

FIG. 8C is a representative lengthwise cross section view of the alternate embodiment of the deflectable end portion 106' of the non-deforming deflectable catheter 100 of the present invention having an embedded coil 130 and notches 107, but without a shim. FIG. 8D is a representative perpendicular cross section view of the deflectable end portion 106' shown in FIG. 8C.

In this alternative embodiment, co-linear transaxially disposed surface notches 107' extend from the outer surface of the catheter jacket or outer jacket of the deflectable distal end portion 106' towards, but not through to pull wire lumen 103. The deflectable portion 106' of the distal end of the catheter or outer jacket comprises at least one notch 107', but is not limited to a single notch and may comprise a plurality of notches, which define at least one initial point of deflection of the catheter. The notch or notches are aligned with pull wire 103 and cause deflection of the deflectable portion within a plane, which essentially contains the central axis of the outer jacket.

The notches 107' can have any of a variety of different cross sectional shapes or profiles as shown in FIG. 8E. In a first alternative, a "V" shape 107A' is used. In another embodiment, a "U" shape 107B' is used. In either of these shapes, the relative depth of the notch 107' can be varied, as can the relative length and/or width of the notch, as noted in 107C' and 107D'. By means of example only, a deeper notch 107' could be used for thicker walls whereas a shallower notch 107' with less depth could be used for a thinner, more flexible deflectable end portion 106' of a catheter 100 of the present invention. Additionally, for example, the notches 107' could be stacked close together, with respect to the lengthwise, axial dimension of the catheter 100, so as to provide a greater number of notches 107' within the same portion of deflectable end portion 106', resulting in a deflectable end 106' capable of forming a finer, more gradual curvature. Additionally, the notches 107' are usually placed transaxially on the deflectable distal portion of the catheter 106', but may also be spaced at a slant or other angle relative to the main, central axis of the elongated catheter 110. It will be understood by those skilled in the art that variations in the size, shape, number, spacing and location of the notches 107' on the deflectable end portion 106' of the catheter 100 is possible and are included in the scope of this invention. It will further be understood that the notched embodiment of catheter 100, shown with a coil, may also contain a shim, or in the alternative may be without either or both the coil and the shim.

Figure 9:
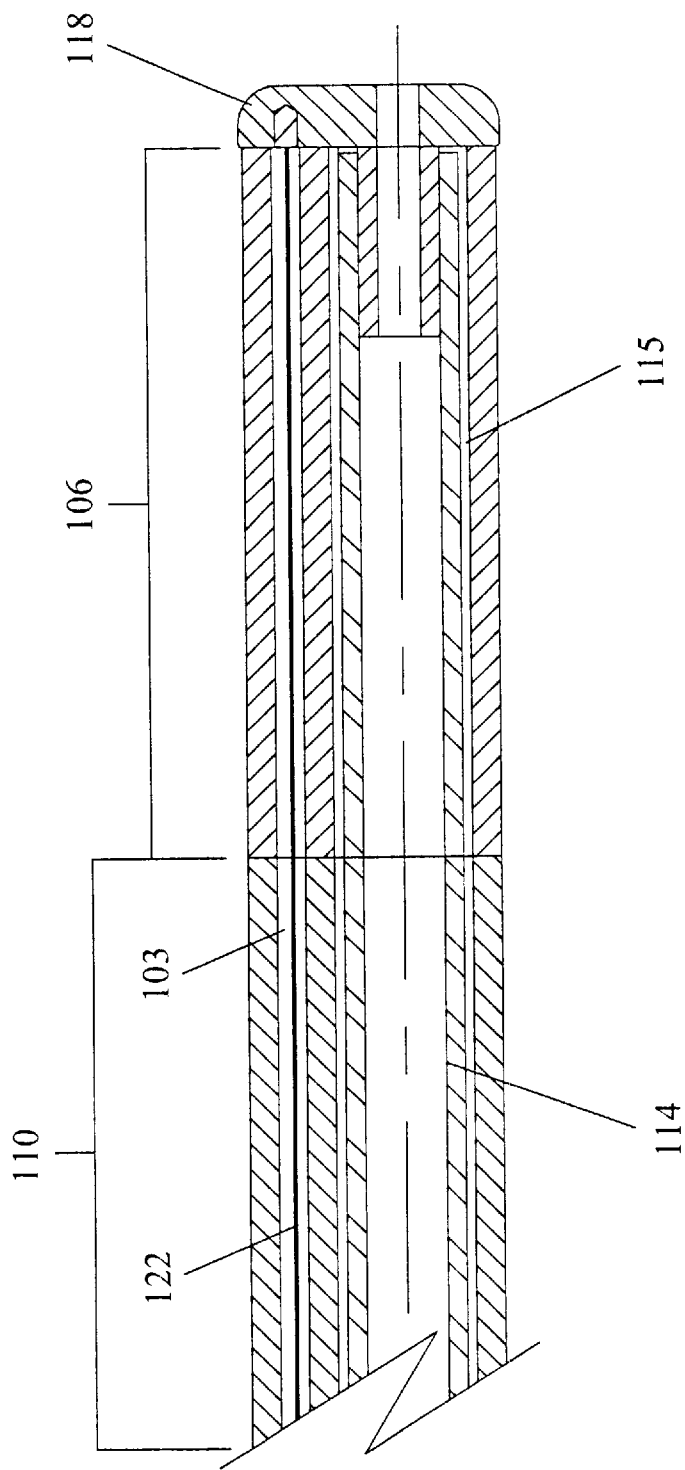
FIG. 9 is a representative side view of an alternate embodiment of the nondeforming deflectable multi lumen catheter of the present invention.

FIG. 9 is a representative side view of an alternate embodiment of the non-deforming deflectable multi lumen catheter of the present invention wherein the pull wire lumen 103 is partially or fully embedded in the wall of the catheter or outer jacket 110 running the entire length of the distal portion of the catheter. In this embodiment, the wall of the inner tube 114 would not house the pull wire lumen 103.

Figure 10:
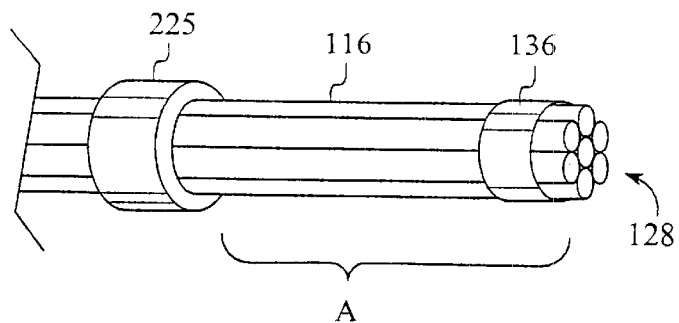
FIG. 10 is a representative isometric view of the distal tip of a functional device, specifically a laser delivery device, for use with and disposed within the catheter of the present invention.

FIG. 10 is a representative isometric view of the distal tip of a functional device, a laser energy delivery device 116, for use with and disposed within the lumen 119 of the catheter of the present invention. Adjacent the distal end 128 of the optical fiber, fiber bundle (as shown) or other laser delivery device, 116, a ring member 225 having a greater diameter than the laser delivery device 116 is attached so as to engage the tip of the catheter 118 and perform as an optional laser energy delivery device displacement stop. Placement of the ring 225 along laser energy delivery device 116 is selected to control depth, as shown by length A, of created pathways into the myocardium. An optional radio opaque marker 136 may be used as well.

Figure 11:
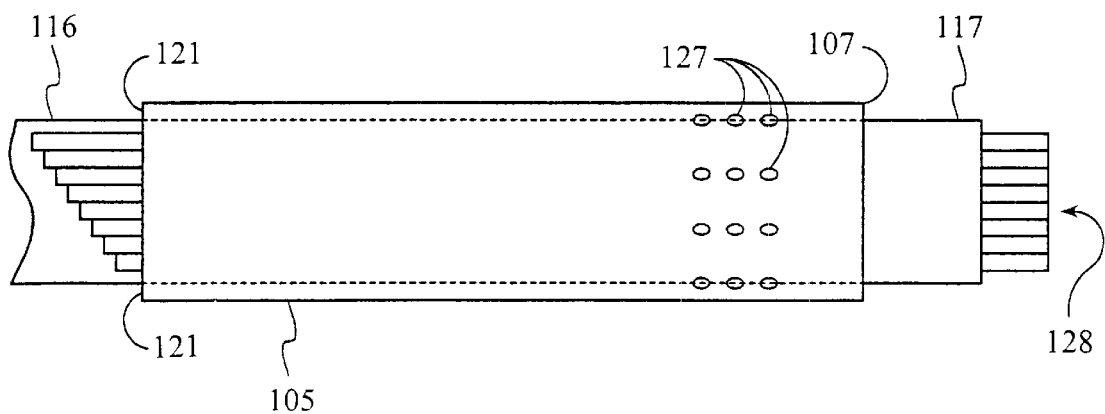
FIG. 11 is a representative side view of an alternate embodiment of functional device, specifically a laser delivery device, adapted for drug delivery for use with and disposed within the catheter of the present invention.

FIG. 11 is a representative side view of an alternate embodiment of a laser delivery device adapted for drug delivery of the deflectable catheter of the present invention. The laser delivery device 116 is disposed within a drug conduit 105. The distal end 107 of the drug conduit 105 has a plurality of (i.e. one or more) perforations 127 formed through the wall of drug conduit 105 allow drugs in space 121 to flow or otherwise be transmitted through drug conduit 105. The distal end 128 of the laser delivery device 116 preferably extends past the distal end 107 of the drug conduit 105. The laser delivery device 116 may consist of a single or bundle of individual optical fibers. A thin plastic tubing material 117, or other tubing material, surrounds the bundle of individual fibers (as shown in FIG. 11), and thus, the combination of tube 117 and drug conduit 105 defines an interstitial drug channel 121 through which drugs can be conveyed through conduit 105 and out the plurality of perforations 127. It will be understood that the tube 117 is optional and may be omitted. In such case, utilizing a single fiber mounted within conduit 105 will result in drug delivery from the plurality of perforations 127 in essentially the same manner as described above. However, in the case of a bundle of fibers without 117, drug solution or other substances will flow around each of the individual fibers of the bundle, thus resulting in percolation of drug out of the drug conduit 105 at either or both the plurality of perforations 127 and the distal end of the fiber bundle. In the embodiment shown, individual perforations 127 are spaced about tube 117. It will be understood that more or fewer perforations may be used, and perforations located at various axial positions located adjacent the distal end 107 of the drug conduit 105.

This is discussed in more detail in U.S. application Ser. No. 08/773,872 entitled LASER MEANS ADAPTED FOR DRUG DELIVERY filed Dec. 27, 1996, and hereby incorporated by reference in its entirety, disclosing a drug delivery apparatus for dispensing a predetermined amount of one or more drugs in, near or around the creation of one or more laser-created openings or channels, particularly PTMR channels and/or stimulation pockets within myocardium or other stimulation zones to stimulate angiogenesis on or in selected target surfaces in the body. The apparatus includes a laser delivery device such as an optical fiber or fiber bundle having one or more conduits for transmitting drugs included as a part of the delivery device. The conduit may comprise a space along a fiber optic cable between an outer jacket of the cable and the fiber optic, or fiber optic bundle, and an aperture or array of apertures in the end of the cable through which the drug escapes. The aperture or apertures can be replaced with a semi-permeable or permeable membrane, strainer, set of leach holes, etc. Or the conduit may be one or more drug tubes contained in the fiber bundle and the drug exits out of the target end surface of the cable. Or the conduit may be one or more tubes between the fiber optic delivery device and the outer jacket. A piercing device may be mounted on the target end of the laser delivery means, or an optical fiber with a pointed tip which pierces the target area prior to applying the laser beam may be used. After or simultaneously with the creation of a laser TMR channel or other opening the drug or drugs are transmitted through the conduit directly into the TMR channel or other opening. The target surface may be mechanically pierced to provide initial access to the target region of tissue, such as myocardium. The drug is dispensed by manually or automatically activating an electric motor which actuates a piston element. This is further shown in U.S. Pat. No. 5,840,059, March et al., entitled THERAPEUTIC AND DIAGNOSTIC AGENT DELIVERY filed Jun. 7, 1995 and issued Nov. 24, 1998, incorporated herein in its entirety.

Figure 12:
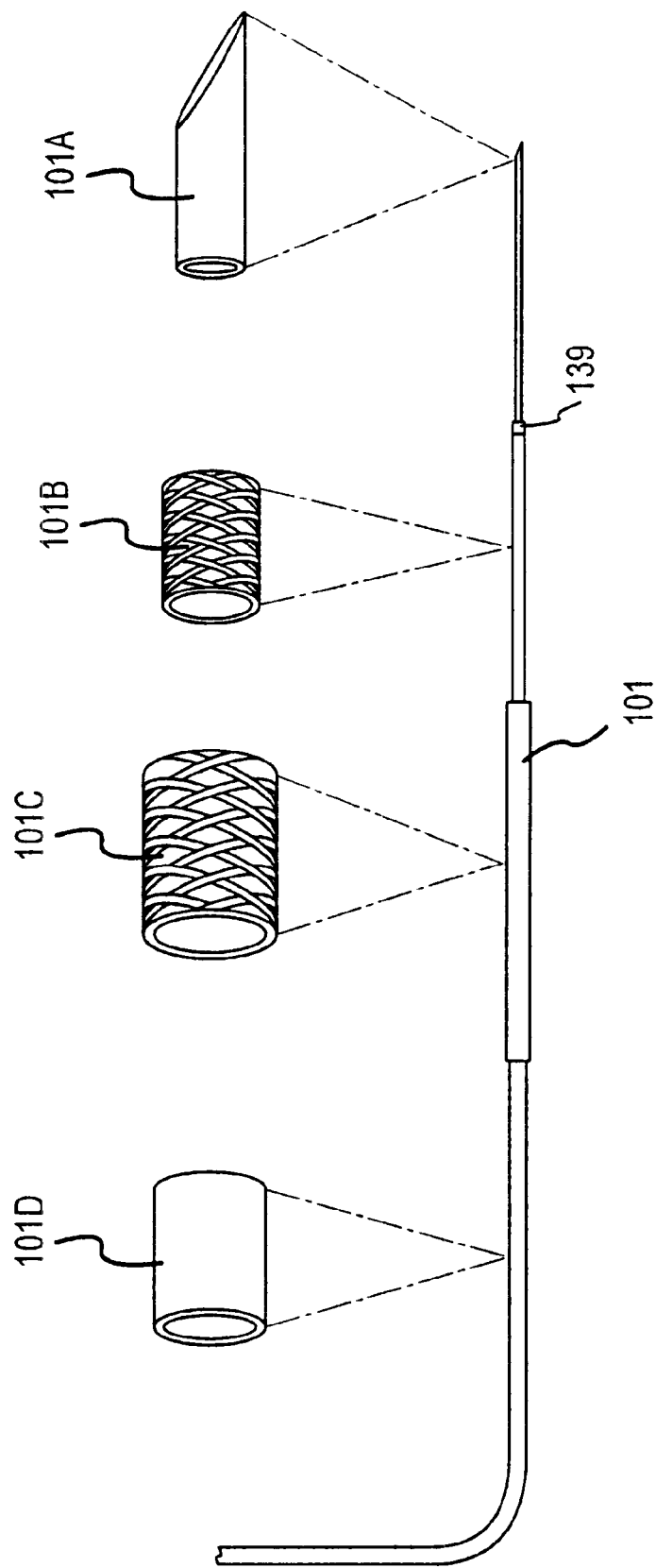
FIG. 12 is a representative isometric detail view of an alternate embodiment of a functional device, specifically a drug delivery tube, for use with and disposed within catheter of the present invention.

Preferably the delivery tube of the present invention is a single, flexible, pushable and torqueable tubing of braided polyamide with an attached piercing needle distal end. FIG. 12 is a representative isometric detail view of an alternate embodiment of the drug delivery conduit or tube 101 disposed in inner tube lumen 119. The distal tip of the delivery tube 101 is piercing needle 101A and is extendable from the distal end of the catheter 118. Tip 101A may be used to pierce the endocardium, prior to or simultaneously with the delivery of therapeutic agents to heart tissue, specifically myocardium. Piercing needle 101A is hollow and is comprised of metal or equivalent. The proximal end of piercing needle 101A is coupled to a second section 101B at coupling point 139. Second section 101B, or the distal tube, is formed of dual helix PEBAX™, polyurethane or other equivalent, resilient, semi-flexible material. The composite double helical tubing of metal and plastic provides column strength and increased flexibility from the medial tubing. A third section 101C, or medial tube, is formed of braided polyamide or equivalent material. The composite braided tubing of metal and plastic provides column strength and increased flexibility from the proximal tubing. The remainder of the piercing needle, or proximal tube, is formed of any suitable, tubular material, for example a metal such as stainless steel, which will allow push and torque of the needle without flexure or other undesirable distortion.

Figure 13:
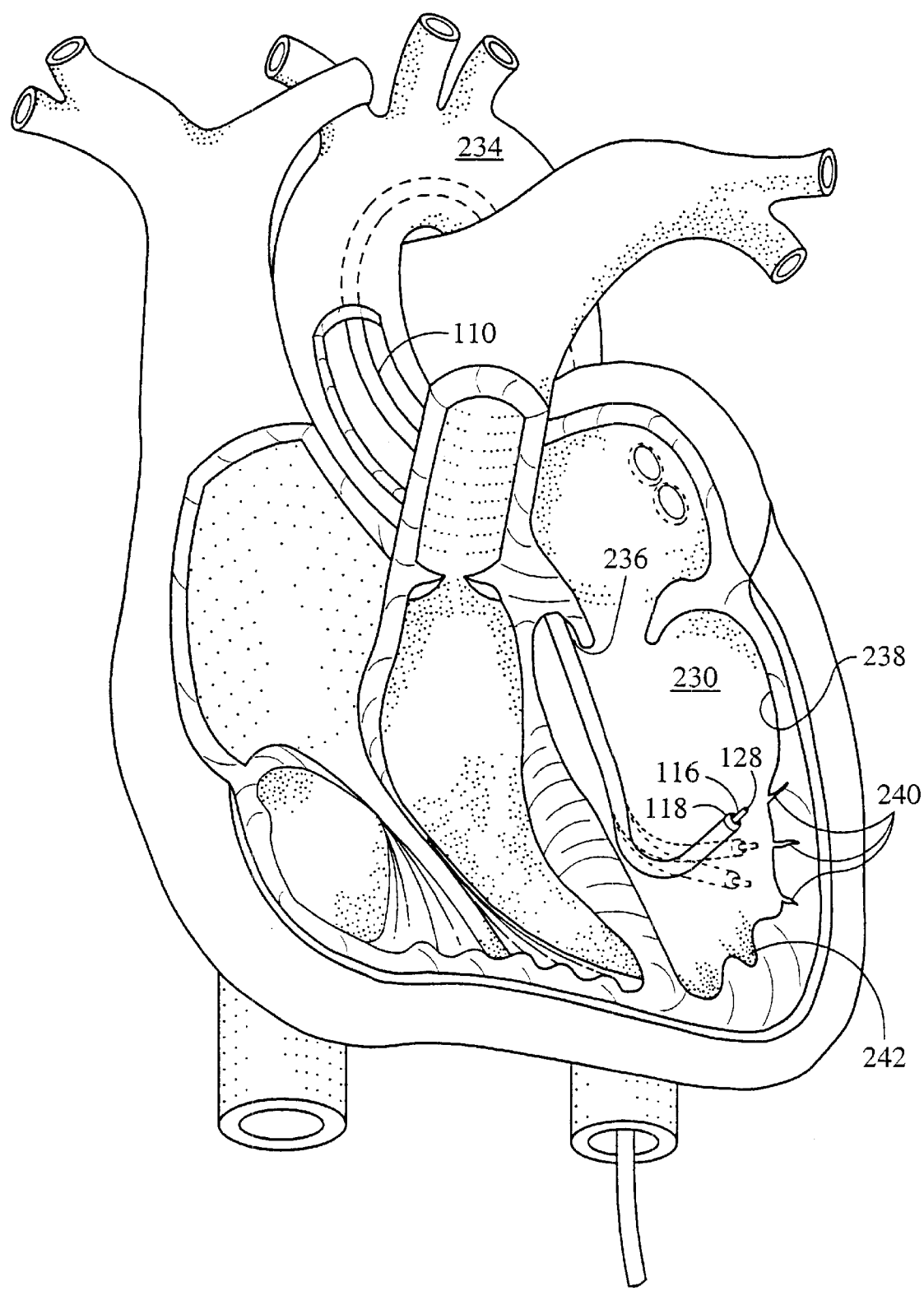
FIG. 13 is a representative perspective view of the deflectable distal portion of the catheter of the present invention within the left ventricle.

FIG. 13 is a representative perspective view of the non-deformable deflectable catheter 100 of the present invention within the left ventricle 230. As indicated above and with regard to the figures, the present invention is directed to catheter systems which are steered into and through parts of the body, such as into the left ventricle, with and without the use of a guide catheter or other guide system. Guide catheter and guidance systems are well known and may be used with the present invention, and therefore are included within the scope of this invention. Typically, entry into the vasculature is made through the femoral artery. A guide wire (not shown) is positioned within the left ventricle 230. The catheter 100 is advanced over the guide wire and into the left ventricle 230. The guide wire is retracted out of the catheter and the functional device, such as an optical fiber, is advanced into position with the catheter.

However, a guide wire or guide catheter need not be used. Alternatively, the distal tip 118 and deflectable end portion 106 of the catheter 100 is inserted into the patient, extended over the aortic arch 234 and prolapsed through the aortic valve 236 into the left ventricle 230. The catheter 100 can be guided into a selected position adjacent a selected surface 238, in this case a portion of endocardium. As the actuator 156 is rotated, deflection of the deflectable portion 106 results in slight modification of the dimension of the elongated portion 110 of the catheter 100, the modification compensated for by the differential screw mechanism of the present invention. Furthermore, a wall contact detection system provides wall contact and contact pressure information to the physician.

Thus, by sequential deflection the deflectable end portion 106 of the catheter 100 and/or by rotation of the catheter 100, extending the distal end 128 of a laser delivery device 116, drug delivery device 101 or other functional device there through, delivering laser energy or performing other therapy, visualization or diagnostic procedures, and retracting the distal end 128 of the laser delivery device 116, drug delivery device 101 or other functional device back into the deflectable end portion 106, the catheter 100 can treat a series of individual, selected treatment points 240 of tissue such as endocardium. Such treatment points 240 would typically be TMR channels or stimulation sites.

Alternatively, retro-lasing can be performed. This novel method includes the steps of advancing the distal tip 128 of laser delivery device 116 a selected distance into the myocardium and then delivering laser energy to create a TMR channel or other treatment site while simultaneously retracting the fiber, laser delivery device 116 or other functional device. With this procedure, with regard to TMR especially, inasmuch as laser energy is only delivered during retraction of the fiber, the possibility of advancing the fiber too far and lasing through an epicardial surface is decreased, and the risks of complications arising from such epicardial perforations, including but not limited to cardiac tamponade (a buildup of pressure in the pericardial sac caused by the presence of an excess of fluid such as blood), proliferation of adhesions between the epicardium and the pericardial sac (thereby preventing normal, frictionless enclosure of the heart muscle within the pericardial sac), etc. are minimized.

The functional device or devices of the present invention includes those devices for treatment and diagnosis of affected organs, tissues or interiors or interior surfaces of the body, including devices configurable and extendable through one or more lumens within the catheter, for example, energy delivery devices, such as laser optical fiber elements, with or with out a piercing needle, laser wave guides, radio frequency tissue ablation devices, microwave cutters, ultrasound transmitters, mechanical coring devices, fluid jets, or drug delivery devices, with or without a piercing needle assembly.

Furthermore, adjunct use of ancillary drug delivery apparatus', blood seal devices, depth stop apparatus such as clamps, bushings, etc., visualization devices, or marker devices as well as other hardware and methodology will be considered within the scope of the present invention.

The alignment mechanism or tip alignment mechanism or automatic tip alignment mechanism of the catheter can be any relative movement compensation mechanism, including, but not limited to, a screw mechanism, for example, a rotatable differential screw mechanism, gear, camming or threaded mechanism.

The present invention is intended for use with any medical laser. In particular, the Holmium or excimer laser is particularly suited to the present invention. However, any suitable laser source, pulsed or otherwise, could provide laser energy to the laser delivery device of the present invention for performing the method of the present invention. Likewise, the catheter and equipment, including laser delivery device, referred to in the present document as well as that known and used in medicine and other disciplines today and in the future, will be included in the scope of this disclosure. Such laser delivery devices include, but are not limited to, individual optical fibers as well as bundles of fibers with and without piercing tips and with or without firing tips or fiber ends having shaped or contoured end faces for selectively diverging the laser beam or other laser energy diverging device, rods, mirrors configurations and other laser delivery device with and without focusing lens and the like. It will also be understood that the catheter and method of the present invention as described herein including the novel combination or use with of any conventional mechanism or method which are known to those skilled in the art, are included within the scope of this invention.

Furthermore, with regard to non-laser TMR, a cannula or trocar assembly may be extended into the tissue of the left ventricle, with or without use of a mechanical piercing tool.

For the purposes of the present invention and disclosure herein, the term "drug" or "drugs" includes any and all drugs and therapeutic agents for use or useable within or on the body, including, but not limited to the following, gene therapies, angiogenic agents, antibiotics, vaccines, function regulators, anti-arrhythmic drugs, growth factors, anticoagulant antagonists, anticoagulants, anti-fibrinolytics, platelet inhibitors, thrombolytics, antihistamines, anti-inflammatory agents, immunosuppressives, receptor antagonists, adrenergic blockers, adrenergic stimulants, alphalbeta adrenergic blockers, angiotensin converting enzyme inhibitors, angiotensin II receptor antagonists, anti-arrhythmics Group I, Group II, Group III, Group IV, beta blockers, calcium channel blockers, diuretics, hypertensive emergency agents, angiogenic agents, FGF-1, FGF-2, EGF, Vascular Endothelial Growth Factor (VEGF) (preclinical), inotropic agents, patent ductus arteriosus therapy, Rauwolfia derivatives and combinations, vasodilators, vasopressors, adjuncts, androgen inhibitors, antibiotic derivatives, anti-estrogens, antimetabolites, cytotoxic agents, enzyme inhibitors, hormones, immunomodulators, nitrogen mustard derivatives, agents used in photodynamic therapy, such as photo-active or photolabile compounds, and/or other materials for performing functions including flushing and cooling, stimulating other responses, detection, analysis, monitoring, visualization or control, etc., said solutions comprising waters, saline and the like, solid and semi-solid materials, and in any forms including capsules and granules, implants, etc.

The present invention includes the delivery of liquid, solid or semi-solid, time release formulations, etc. It will be understood that there are additional drugs or therapeutic agents which may become useful, such as agents directed at bone or implanted in semi-permeable sacs, radioisotopes, and future gene therapies which are also included in the scope of this invention.

Active compounds which are given systemically have a normal therapeutic window which can be expressed as mg of drug per kg of body weight. The amount of agent which is therapeutically acceptable when administering a drug locally can be approximated as mg of drug per kg of target treatment area (e.g. organ weight), optimized accordingly with consideration of toxicity and mechanism of drug action. Agents delivered to a specific site can achieve high local concentrations at the delivery point. Optimal drug dose may scale differently when the drug is administered locally rather than systemically. Thus, the amount of a given agent that should be delivered in order to achieve a therapeutic effect must be optimized accordingly with consideration of toxicity levels (both locally and systemically), mechanism of drug action, drug clearance mechanisms, and drug diffusion levels.

It will further be understood that while the present invention has been described for performing TMR on endocardial surfaces in the left ventricle, the apparatus and methods described herein are equally intended for use in any suitable procedure, including but not limited to procedures, where any device need be extended through a guide catheter or the vasculature to an opening or other point within the body for other medical procedures including one or more of the following, laser treatment, drug delivery, visualization, biopsy, etc. Stimulation, for example, is performed by using laser energy to create zones or pockets, optionally interconnected at least initially by small channels ablated through the tissue, for the introduction of blood born growth and healing factors and stimulated capillary growth surrounding the lased zones or pockets to create an increased supply of oxygen to the tissue and thus a revitalization of the heart muscle. Methods and apparatus for causing stimulation are more fully described in co-pending U.S. patent application Ser. No. 08/664,956 filed Jun. 13, 1996, herein incorporated by reference.

While the principles of the invention have been made clear in illustrative embodiments, there will be immediately obvious to those skilled in the art many modifications of structure, arrangement, proportions, the elements, materials, and components used in the practice of the invention, and otherwise, which are particularly adapted to specific environments and operative requirements without departing from those principles. The appended claims are intended to cover and embrace any and all such modifications, with the limits only of the true spirit and scope of the invention.

We claim:

1. A non-deforming catheter apparatus comprising:

a deflection and translation mechanism;

a hollow outer jacket having a deflectable distal portion and an at least partially embedded pull wire lumen and coupled at a proximal end to the deflection and translation mechanism;

a tip coupled to a distal end of the outer jacket;

an inner tube with lumen in the hollow of the outer jacket;

at least one functional device disposed in the lumen having a distal end extendable from the tip of the catheter;

a pull wire contained in the pull wire lumen having a distal end coupled to the tip and a proximal end coupled to the deflection mechanism, said pull wire effecting non-deforming deflection of the deflectable distal portion of the outer jacket and functional device therein by movement of the deflection mechanism, wherein the deflectable portion bends up to about 270 degrees;

a coil embedded in the deflectable portion of the outer jacket;

one or more notches in an outer surface of the outer jacket and aligned with the pull wire in which the pull wire lumen has a proximal end embedded in the inner tube and a distal end at least partially embedded in the deflectable distal portion of the outer jacket; and a relative movement compensation mechanism for maintaining alignment between the outer jacket and the functional device coupled to the deflection mechanism whereby movement of the deflection mechanism causes simultaneous movement of the relative movement compensation mechanism.

2. The apparatus of claim 1 wherein the outer jacket is comprised of one or more polymers having one or more flexibility.

3. The apparatus of claim 2 wherein the proximal end of the outer jacket further comprises a braided construction.

4. The apparatus of claim 3 wherein a distal portion of the apparatus comprises one or more radio opaque materials.

5. The apparatus of claim 4 wherein the functional device is a laser energy delivery device.

6. The apparatus of claim 5 wherein the functional device further comprises a drug delivery device in combination with the laser energy delivery device.

7. The apparatus of claim 1 wherein the outer jacket is comprised of one or more polymers of having one or more flexibility.

8. The apparatus of claim 7 wherein the proximal end of the outer jacket further comprises a braided construction.

9. The apparatus of claim 8 wherein a distal portion of the apparatus comprises one or more radio opaque materials.

10. The apparatus of claim 9 wherein the functional device is a laser energy delivery device.

11. The apparatus of claim 10 wherein the functional device further comprises a drug delivery device in combination with the laser energy delivery device.

12. A non-deforming catheter apparatus comprising:

a deflection and translation mechanism;

a hollow outer jacket having a deflectable distal portion and an at least partially embedded pull wire lumen and coupled at a proximal end to the deflection and translation mechanism;

a tip coupled to a distal end of the outer jacket;

an inner tube with lumen in the hollow of the outer jacket;

at least one functional device disposed in the lumen having a distal end extendable from the tip of the catheter;

a pull wire contained in the pull wire lumen having a distal end coupled to the tip and a proximal end coupled to the deflection mechanism, said pull wire effecting non-deforming deflection of the deflectable distal portion of the outer jacket and functional device therein by movement of the deflection mechanism, wherein the deflectable portion bends up to about 270 degrees;

a coil embedded in the deflectable portion of the outer jacket;

one or more notches in an outer surface of the outer jacket and aligned with the pull wire; and a relative movement compensation mechanism for maintaining alignment between the outer jacket and the functional device coupled to the deflection mechanism whereby movement of the deflection mechanism causes simultaneous movement of the relative movement compensation mechanism.

13. The apparatus of claim 12 wherein the outer jacket is comprised of one or more polymers of having one or more flexibility.

14. The apparatus of claim 13 wherein the proximal end of the outer jacket further comprises a braided construction.

15. The apparatus of claim 14 wherein a distal portion of the apparatus comprises one or more radio opaque materials.

16. The apparatus of claim 15 wherein the functional device is a laser energy delivery device.

17. The apparatus of claim 16 wherein the functional device further comprises a drug delivery device in combination with the laser energy delivery device.

18. The apparatus of claim 12 wherein the outer jacket is comprised of one or more polymers of having one or more flexibility.

19. The apparatus of claim 18 wherein the proximal end of the outer jacket further comprises a braided construction.

20. The apparatus of claim 19 wherein a distal portion of the apparatus comprises one or more radio opaque materials.

21. The apparatus of claim 20 wherein the functional device is a laser energy delivery device.

22. The apparatus of claim 21 wherein the functional device further comprises a drug delivery device in combination with the laser energy delivery device.

23. The apparatus of claim 12 further comprising an at least partially embedded shim in the deflectable portion of the outer jacket.

24. The apparatus of claim 23 wherein the pull wire lumen has a proximal end embedded in the inner tube and a distal end at least partially embedded in the deflectable distal portion of the outer jacket.

25. A non-deforming catheter apparatus comprising:

a deflection and translation mechanism;

a hollow outer jacket having a deflectable distal portion and an at least partially embedded pull wire lumen and coupled at a proximal end to the deflection and translation mechanism;

a tip coupled to a distal end of the outer jacket;

an inner tube with lumen in the hollow of the outer jacket;

at least one functional device disposed in the lumen having a distal end extendable from the tip of the catheter;

a pull wire contained in the pull wire lumen having a distal end coupled to the tip and a proximal end coupled to the deflection mechanism, said pull wire effecting non-deforming deflection of the deflectable distal portion of the outer jacket and functional device therein by movement of the deflection mechanism, wherein the deflectable portion bends up to about 270 degrees; and a coil embedded in the deflectable portion of the outer jacket;

wherein the translation mechanism is coupled to a drug delivery module, the functional device is a drug delivery tube with a piercing needle coupled to a distal end and further comprising a relative movement compensation mechanism for maintaining alignment between the outer jacket and the drug delivery tube coupled to the deflection mechanism whereby movement of the deflection mechanism causes simultaneous movement of the relative movement compensation mechanism.

26. The apparatus of claim 25 wherein the drug delivery tube is comprised of one or more polymers having one or more flexibility.

27. The apparatus of claim 26 wherein at least a portion of the drug delivery tube comprises a braided construction.

28. The apparatus of claim 25 further comprising a relative movement compensation mechanism for maintaining alignment between the outer jacket and the functional device coupled to the deflection mechanism whereby movement of the deflection mechanism causes simultaneous movement of the relative movement compensation mechanism.

29. The apparatus of claim 28 wherein the outer jacket is comprised of one or more polymers having one or more flexibility.

30. The apparatus of claim 29 wherein the proximal end of the outer jacket further comprises a braided construction.

31. The apparatus of claim 30 wherein a distal portion of the apparatus comprises one or more radio opaque materials.

32. The apparatus of claim 31 wherein the functional device is a laser energy delivery device.

33. The apparatus of claim 32 wherein the functional device further comprises a drug delivery device in combination with the laser energy delivery device.

34. The apparatus of claim 25 wherein the outer jacket is comprised of one or more polymers having one or more flexibility.

35. The apparatus of claim 34 wherein the proximal end of the outer jacket further comprises a braided construction.

36. The apparatus of claim 35 wherein a distal portion of the apparatus comprises one or more radio opaque materials.

37. The apparatus of claim 36 wherein the functional device is a laser energy delivery device.

38. The apparatus of claim 37 wherein the functional device further comprises a drug delivery device in combination with the laser energy delivery device.

39. The apparatus of claim 25 further comprising a relative movement compensation mechanism for maintaining alignment between the outer jacket and the functional device coupled to the deflection mechanism whereby movement of the deflection mechanism causes simultaneous movement of the relative movement compensation mechanism.

40. The apparatus of claim 39 wherein the outer jacket is comprised of one or more polymers having one or more flexibility.

41. The apparatus of claim 40 wherein the proximal end of the outer jacket further comprises a braided construction.

42. The apparatus of claim 41 wherein a distal portion of the apparatus comprises one or more radio opaque materials.

43. The apparatus of claim 42 wherein the functional device is a laser energy delivery device.

44. The apparatus of claim 43 wherein the functional device further comprises a drug delivery device in combination with the laser energy delivery device.

45. The apparatus of claim 25 wherein the outer jacket is comprised of one or more polymers having one or more flexibility.

46. The apparatus of claim 45 wherein the proximal end of the outer jacket further comprises a braided construction.

47. The apparatus of claim 46 wherein a distal portion of the apparatus comprises one or more radio opaque materials.

48. The apparatus of claim 47 wherein the functional device is a laser energy delivery device.

49. The apparatus of claim 48 wherein the functional device further comprises a drug delivery device in combination with the laser energy delivery device.

50. The apparatus of claim 25 further comprising one or more notches in an outer surface of the outer jacket and aligned with the pull wire.

51. A non-deforming catheter apparatus comprising:
a deflection and translation mechanism;
a hollow outer jacket having a deflectable distal portion and an at least partially embedded pull wire lumen and coupled at a proximal end to the deflection and translation mechanism;
a tip coupled to a distal end of the outer jacket;
an inner tube with lumen in the hollow of the outer jacket;
at least one functional device disposed in the lumen having a distal end extendable from the tip of the catheter;
a pull wire contained in the pull wire lumen having a distal end coupled to the tip and a proximal end coupled to the deflection mechanism, said pull wire effecting non-deforming deflection of the deflectable distal portion of the outer jacket and functional device therein by movement of the deflection mechanism, wherein the deflectable portion bends up to about 270 degrees; and
one or more notches in an outer surface of the outer jacket and aligned with the pull wire;
wherein the pull wire lumen has a proximal end embedded in the inner tube and a distal end at least partially embedded in the deflectable distal portion of the outer jacket.

52. The apparatus of claim 51 further comprising a relative movement compensation mechanism for maintaining alignment between the outer jacket and the functional device coupled to the deflection mechanism whereby movement of the deflection mechanism causes simultaneous movement of the relative movement compensation mechanism.

53. The apparatus of claim 52 wherein the outer jacket is comprised of one or more polymers having one or more flexibility.

54. The apparatus of claim 53 wherein the proximal end of the outer jacket further comprises a braided construction.

55. The apparatus of claim 54 wherein a distal portion of the apparatus comprises one or more radio opaque materials.

56. The apparatus of claim 55 wherein the functional device is a laser energy delivery device.

57. The apparatus of claim 56 wherein the functional device further comprises a drug delivery device in combination with the laser energy delivery device.

58. The apparatus of claim 51 wherein the outer jacket is comprised of one or more polymers having one or more flexibility.

59. The apparatus of claim 58 wherein the proximal end of the outer jacket further comprises a braided construction.

60. The apparatus of claim 59 wherein a distal portion of the apparatus comprises one or more radio opaque materials.

61. The apparatus of claim 60 wherein the functional device is a laser energy delivery device.

62. The apparatus of claim 61 wherein the functional device further comprises a drug delivery device in combination with the laser energy delivery device.

63. The apparatus of claim 51 further comprising a relative movement compensation mechanism for maintaining alignment between the outer jacket and the functional device coupled to the deflection mechanism whereby movement of the deflection mechanism causes simultaneous movement of the relative movement compensation mechanism.

64. The apparatus of claim 63 wherein the outer jacket is comprised of one or more polymers having one or more flexibility.

65. The apparatus of claim 64 wherein the proximal end of the outer jacket further comprises a braided construction.

66. The apparatus of claim 65 wherein a distal portion of the apparatus comprises one or more radio opaque materials.

67. The apparatus of claim 66 wherein the functional device is a laser energy delivery device.

68. The apparatus of claim 67 wherein the functional device further comprises a drug delivery device in combination with the laser energy delivery device.

69. The apparatus of claim 51 wherein the outer jacket is comprised of one or more polymers having one or more flexibility.

70. The apparatus of claim 69 wherein the proximal end of the outer jacket further comprises a braided construction.

71. The apparatus of claim 70 wherein a distal portion of the apparatus comprises one or more radio opaque materials.

72. The apparatus of claim 71 wherein the functional device is a laser energy delivery device.

73. The apparatus of claim 72 wherein the functional device further comprises a drug delivery device in combination with the laser energy delivery device.

* * * * *